United States Patent
Wiley et al.

(10) Patent No.: US 9,283,075 B2
(45) Date of Patent: *Mar. 15, 2016

(54) SHOULDER ARTHROPLASTY SYSTEM

(75) Inventors: Roy C. Wiley, Warsaw, IN (US); Brian C. Hodorek, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 491 days.

This patent is subject to a terminal disclaimer.

(21) Appl. No.: 13/616,154

(22) Filed: Sep. 14, 2012

(65) Prior Publication Data
US 2013/0006369 A1  Jan. 3, 2013

Related U.S. Application Data

(60) Continuation of application No. 12/777,862, filed on May 11, 2010, now Pat. No. 8,940,054, which is a division of application No. 11/624,342, filed on Jan. 18, 2007, now Pat. No. 7,854,768.

(60) Provisional application No. 60/805,012, filed on Jun. 16, 2006, provisional application No. 60/760,897, filed on Jan. 20, 2006.

(51) Int. Cl.
*A61F 2/40* (2006.01)
*A61F 2/30* (2006.01)
(Continued)

(52) U.S. Cl.
CPC ............. *A61F 2/30734* (2013.01); *A61F 2/40* (2013.01); *A61B 17/8047* (2013.01); *A61B 17/842* (2013.01); *A61B 17/86* (2013.01);
(Continued)

(58) Field of Classification Search
CPC .............................................. A61F 2002/4022

USPC ................. 623/19.11–19.14, 22.24, 22.28
See application file for complete search history.

(56) References Cited

U.S. PATENT DOCUMENTS 3,815,157 A 6/1974 Skorecki et al.
3,842,442 A 10/1974 Kolbel
(Continued)

FOREIGN PATENT DOCUMENTS

AU 714659 B2 10/1996
AU 199655397 B2 10/1996
(Continued)

OTHER PUBLICATIONS

Translation of EP299889A2 retrieved from espacenet on Apr. 21, 2015.*

(Continued)

*Primary Examiner* — Thomas J Sweet
*Assistant Examiner* — Megan Wolf
(74) *Attorney, Agent, or Firm* — Schwegman Lundberg & Woessner, P.A.

(57) ABSTRACT

An implant system for total shoulder arthroplasties, hemi shoulder arthroplasties, and "reverse" total shoulder arthroplasties including a humeral stem having an enlarged head portion with interfaces adapted to removably receive various modular interchangeable components, such as articulating liners, spacers, and adapter inserts. The humeral stem functions as a universal platform that may be used in either conventional or "reverse" total shoulder arthroplasties, as well as hemi shoulder arthroplasties, and may remain implanted in place during a revision in which the implant system is converted between the foregoing configurations, for example.

30 Claims, 22 Drawing Sheets

(51) Int. Cl.
 *A61B 17/80* (2006.01)
 *A61B 17/84* (2006.01)
 *A61B 17/86* (2006.01)
 *A61F 2/46* (2006.01)

(52) U.S. Cl.
 CPC ........ *A61F 2/4684* (2013.01); *A61F 2002/305* (2013.01); *A61F 2002/3092* (2013.01); *A61F 2002/30332* (2013.01); *A61F 2002/30367* (2013.01); *A61F 2002/30578* (2013.01); *A61F 2002/30607* (2013.01); *A61F 2002/30616* (2013.01); *A61F 2002/30772* (2013.01); *A61F 2002/30878* (2013.01); *A61F 2002/4011* (2013.01); *A61F 2002/4022* (2013.01); *A61F 2002/4037* (2013.01); *A61F 2002/4051* (2013.01); *A61F 2002/4085* (2013.01); *A61F 2002/4641* (2013.01); *A61F 2220/0025* (2013.01); *A61F 2220/0033* (2013.01); *A61F 2250/0062* (2013.01); *A61F 2310/00491* (2013.01); *A61F 2310/00544* (2013.01)

(56) References Cited

U.S. PATENT DOCUMENTS

| | | |
|---|---|---|
| 3,863,273 A | 2/1975 | Averill |
| 3,869,730 A | 3/1975 | Skobel |
| 3,916,451 A | 11/1975 | Buechel et al. |
| 3,978,528 A | 9/1976 | Crep |
| 4,030,143 A | 6/1977 | Elloy et al. |
| 4,040,131 A | 8/1977 | Gristina |
| 4,180,873 A | 1/1980 | Fixel |
| 4,206,517 A | 6/1980 | Pappas et al. |
| 4,645,450 A | 2/1987 | West |
| 4,693,723 A | 9/1987 | Gabard |
| 4,822,370 A | 4/1989 | Schelhas |
| 4,919,669 A | 4/1990 | Lannelongue |
| 4,964,865 A | 10/1990 | Burkhead et al. |
| 5,049,158 A | 9/1991 | Engelhardt |
| 5,080,673 A | 1/1992 | Burkhead et al. |
| 5,092,897 A | 3/1992 | Forte |
| 5,133,764 A | 7/1992 | Pappas et al. |
| 5,282,861 A | 2/1994 | Kaplan |
| 5,314,479 A | 5/1994 | Rockwood, Jr. et al. |
| 5,358,526 A | 10/1994 | Tornier |
| 5,358,536 A | 10/1994 | Koshida et al. |
| 5,429,639 A | 7/1995 | Judet |
| 5,462,563 A | 10/1995 | Shearer et al. |
| 5,489,309 A * | 2/1996 | Lackey et al. ............. 623/19.14 |
| 5,520,690 A | 5/1996 | Errico et al. |
| 5,531,746 A | 7/1996 | Errico et al. |
| 5,534,027 A | 7/1996 | Hodorek |
| 5,549,682 A | 8/1996 | Roy |
| 5,607,426 A | 3/1997 | Ralph et al. |
| 5,643,265 A | 7/1997 | Errico et al. |
| 5,645,607 A | 7/1997 | Hickey |
| 5,647,873 A | 7/1997 | Errico et al. |
| 5,669,911 A | 9/1997 | Errico et al. |
| 5,690,630 A | 11/1997 | Errico et al. |
| 5,702,457 A | 12/1997 | Walch et al. |
| 5,702,486 A | 12/1997 | Craig et al. |
| 5,723,018 A | 3/1998 | Cyprien et al. |
| 5,725,588 A | 3/1998 | Errico et al. |
| 5,817,094 A | 10/1998 | Errico et al. |
| 5,876,402 A | 3/1999 | Errico et al. |
| 5,888,204 A | 3/1999 | Ralph et al. |
| 6,045,582 A | 4/2000 | Prybyla |
| 6,139,550 A | 10/2000 | Michelson |
| 6,187,012 B1 | 2/2001 | Masini |
| 6,197,065 B1 | 3/2001 | Martin et al. |
| 6,206,925 B1 | 3/2001 | Tornier |
| 6,334,874 B1 | 1/2002 | Tornier et al. |
| RE37,665 E | 4/2002 | Ralph et al. |
| 6,558,387 B2 | 5/2003 | Errico et al. |
| 6,589,282 B2 | 7/2003 | Pearl |
| 6,673,115 B2 | 1/2004 | Resch et al. |
| 6,679,916 B1 | 1/2004 | Frankle et al. |
| 6,761,740 B2 | 7/2004 | Tornier |
| 6,790,234 B1 | 9/2004 | Frankle |
| 6,863,690 B2 | 3/2005 | Ball et al. |
| 6,887,277 B2 | 5/2005 | Rauscher et al. |
| 6,899,736 B1 | 5/2005 | Rauscher |
| 6,953,478 B2 | 10/2005 | Bouttens et al. |
| 7,011,686 B2 | 3/2006 | Ball et al. |
| 7,175,663 B1 | 2/2007 | Stone |
| 7,854,768 B2 | 12/2010 | Wiley et al. |
| 8,303,665 B2 | 11/2012 | Tornier et al. |
| 8,940,054 B2 | 1/2015 | Wiley et al. |
| 2001/0011193 A1 | 8/2001 | Nogarin |
| 2003/0097183 A1 | 5/2003 | Rauscher et al. |
| 2003/0114933 A1 | 6/2003 | Bouttens et al. |
| 2003/0158605 A1 | 8/2003 | Tornier |
| 2004/0064190 A1 | 4/2004 | Ball et al. |
| 2004/0094187 A1 | 5/2004 | Lee |
| 2004/0220673 A1 | 11/2004 | Pria |
| 2004/0220674 A1 | 11/2004 | Pria |
| 2004/0230311 A1 | 11/2004 | Cyprien et al. |
| 2005/0065612 A1 | 3/2005 | Winslow |
| 2005/0071014 A1 | 3/2005 | Barnett et al. |
| 2005/0107882 A1 | 5/2005 | Stone et al. |
| 2005/0113931 A1 | 5/2005 | Horber |
| 2005/0165490 A1 | 7/2005 | Tornier |
| 2005/0251263 A1 | 11/2005 | Forrer et al. |
| 2005/0256583 A1 | 11/2005 | Bouttens et al. |
| 2005/0261775 A1 | 11/2005 | Baum et al. |
| 2005/0278030 A1 | 12/2005 | Tornier et al. |
| 2005/0278031 A1 | 12/2005 | Tornier et al. |
| 2005/0278033 A1 | 12/2005 | Tornier et al. |
| 2006/0020344 A1 | 1/2006 | Shultz et al. |
| 2006/0069445 A1 | 3/2006 | Ondrla et al. |
| 2006/0149388 A1 | 7/2006 | Smith et al. |
| 2006/0200248 A1 | 9/2006 | Beguin et al. |
| 2007/0173945 A1 | 7/2007 | Wiley et al. |
| 2008/0228281 A1 | 9/2008 | Forrer et al. |
| 2008/0294268 A1 | 11/2008 | Baum et al. |
| 2010/0222886 A1 | 9/2010 | Wiley et al. |

FOREIGN PATENT DOCUMENTS

| | | |
|---|---|---|
| CA | 2216955 C | 2/2004 |
| CA | 2631580 A1 | 7/2007 |
| CH | 426096 A | 12/1966 |
| DE | 2903366 A1 | 8/1979 |
| DE | 2903366 B2 | 11/1980 |
| DE | 3306151 A1 | 9/1983 |
| DE | 4128259 A1 | 3/1993 |
| DE | 19548154 A2 | 6/1997 |
| EP | 0065482 A2 | 11/1982 |
| EP | 0066092 A1 | 12/1982 |
| EP | 0144209 A1 | 6/1985 |
| EP | 0190093 A1 | 8/1986 |
| EP | 0298234 A1 | 1/1989 |
| EP | 0299889 A2 | 1/1989 |
| EP | 299889 A2 * | 1/1989 ................ A61F 2/40 |
| EP | 0339530 A2 | 11/1989 |
| EP | 0445068 A1 | 9/1991 |
| EP | 0549480 A1 | 6/1993 |
| EP | 0583711 A2 | 2/1994 |
| EP | 0611008 A1 | 8/1994 |
| EP | 0640324 A1 | 3/1995 |
| EP | 0679375 A1 | 11/1995 |
| EP | 0715836 A1 | 6/1996 |
| EP | 0853928 A1 | 7/1998 |
| EP | 0679375 B1 | 8/1998 |
| EP | 0927548 A2 | 7/1999 |
| EP | 0953321 A1 | 11/1999 |
| EP | 1004283 A2 | 5/2000 |
| EP | 1064890 A | 1/2001 |
| EP | 0828459 B1 | 9/2003 |
| EP | 1380274 A1 | 1/2004 |
| EP | 1415621 A2 * | 5/2004 ................ A61F 2/40 |
| EP | 1472999 A1 | 11/2004 |
| EP | 1488764 A1 | 12/2004 |

(56) References Cited

FOREIGN PATENT DOCUMENTS

| | | | |
|---|---|---|---|
| EP | 1004283 B1 | 5/2005 |
| EP | 1543801 A1 | 6/2005 |
| EP | 1364623 B1 | 10/2005 |
| EP | 1591084 A1 | 11/2005 |
| EP | 1598034 A1 | 11/2005 |
| EP | 1393697 B1 | 2/2006 |
| EP | 1543801 B1 | 8/2007 |
| EP | 1983940 B1 | 3/2014 |
| FR | 2519545 A1 | 7/1983 |
| FR | 2522090 A1 | 8/1983 |
| FR | 2545352 A1 | 11/1984 |
| FR | 2579454 A1 | 10/1986 |
| FR | 2617040 A1 | 12/1988 |
| FR | 2621814 A1 | 4/1989 |
| FR | 2652498 A1 | 4/1991 |
| FR | 2674122 A1 | 9/1992 |
| FR | 2697996 A1 | 5/1994 |
| FR | 2699400 A1 | 6/1994 |
| FR | 2704747 A1 | 11/1994 |
| FR | 2721200 A1 | 12/1995 |
| FR | 2780635 A1 | 1/2000 |
| FR | 2825263 A1 | 12/2002 |
| FR | 2869217 A1 | 10/2005 |
| GB | 1573608 A | 8/1980 |
| GB | 2069338 A | 8/1981 |
| GB | 2297257 A | 7/1996 |
| GB | 2405346 A | 3/2005 |
| JP | 11503351 A | 3/1999 |
| JP | 2004113804 A | 4/2004 |
| JP | 2004121850 A | 4/2004 |
| SU | 749392 A | 7/1980 |
| WO | WO-9002533 A2 | 3/1990 |
| WO | WO-9602203 A1 | 2/1996 |
| WO | WO-9632071 A1 | 10/1996 |
| WO | WO-9725943 A1 | 7/1997 |
| WO | WO-9846172 A1 | 10/1998 |
| WO | WO-0147442 A1 | 7/2001 |
| WO | WO-2005032430 A1 | 4/2005 |

OTHER PUBLICATIONS

"U.S. Appl. No. 11/624,342, Examiner Interview Summary mailed Aug. 25, 2010", 1 pgs.
"U.S. Appl. No. 11/624,342, Final Office Action mailed Aug. 14, 2009", 10 pgs.
"U.S. Appl. No. 11/624,342, Non Final Office Action mailed Feb. 3, 2010", 12 pgs.
"U.S. Appl. No. 11/624,342, Non Final Office Action mailed Aug. 19, 2008", 9 pgs.
"U.S. Appl. No. 11/624,342, Notice of Allowance mailed Aug. 25, 2010", 3 pgs.
"U.S. Appl. No. 11/624,342, Response filed Jan. 8, 2009 to Non Final Office Action mailed Aug. 19, 2008", 12 pgs.
"U.S. Appl. No. 11/624,342, Response filed Jan. 12, 2010 to Final Office Action mailed Aug. 14, 2009", 13 pgs.
"U.S. Appl. No. 11/624,342, Response filed Jun. 23, 2010 to Non Final Office Action mailed Feb. 3, 2010", 17 pgs.
"U.S. Appl. No. 11/624,342, Response filed Jun. 30, 2008 to Restriction Requirement mailed May 21, 2008", 2 pgs.
"U.S. Appl. No. 11/624,342, Restriction Requirement mailed May 21, 2008", 6 pgs.
"U.S. Appl. No. 11/624,342, Supplemental Notice of Allowability mailed Oct. 25, 2010", 2 pgs.
"U.S. Appl. No. 12/777,862, Final Office Action mailed Jun. 24, 2011", 9 pgs.
"U.S. Appl. No. 12/777,862, Non Final Office Action mailed Jan. 19, 2011", 7 pgs.
"U.S. Appl. No. 12/777,862, Preliminary Amendment filed May 11, 2010", 6 pgs.
"U.S. Appl. No. 12/777,862, Response filed Apr. 19, 2011 to Non Final Office Action mailed Jan. 19, 2011", 10 pgs.

"U.S. Appl. No. 12/777,862, Response filed Sep. 14, 2011 to Final Office Action mailed Jun. 24, 2011", 11 pgs.
"Delta CTA Reverse Shoulder System", DuPuy (Delta), Surgical Technique, (2004), 28 pgs.
"European Application Serial No. 07717300.3, Response filed Sep. 26, 2012 to Office Action mailed Feb. 2, 2012", 11 pgs.
"European Application Serial No. 07717300.3, Office Action mailed Feb. 2, 2012", 7 pgs.
"European Application Serial No. 07717300.3, Office Action mailed Mar. 26, 2012", 1 pg.
"European Application Serial No. 07717300.3, Office Action mailed Sep. 5, 2011", 5 pgs.
"European Application Serial No. 07717300.3, Office Action mailed Sep. 16, 2008", 1 pg.
"European Application Serial No. 07717300.3, Office Action mailed Sep. 17, 2008", 2 pgs.
"European Application Serial No. 07717300.3, Office Action mailed Nov. 7, 2012", 4 pgs.
"European Application Serial No. 07717300.3, Response filed Jan. 13, 2012 to Office Action mailed Sep. 5, 2011", 10 pgs.
"International Application Serial No. PCT/US2007/060672, International Preliminary Report on Patentablility mailed on Jul. 22, 2008", 8 pgs.
"International Application Serial No. PCT/US2007/060672, International Search Report mailed Aug. 23, 2007", 6 pgs.
"International Application Serial No. PCT/US2007/060672, Written Opinion mailed Aug. 23, 2007", 7 pgs.
"Japanese Application Serial No. 2008-551524, Office Action mailed Feb. 21, 2012", With English Translation, 12 pgs.
"Japanese Application Serial No. 2008-551524, Response filed Aug. 28, 2012 to Office Action mailed Feb. 28, 2012", 9 pgs.
"ProNews", Publication of Zimmer Group, Swiss Edition, (Mar. 2004), 12 pgs.
"Tornier", [Online.] Retrieved from the Internet: <www.tornier-us.com/product_shidr_aqu.html#>, (accessed Feb. 28, 2007), 1 pg.
Budoff, Jeffrey E, "Reverse Total Shoulder Arthroplasty", [Online.] Retrieved from the Internet: <http://www.bcm.edu/md/budoff/patienteducation/reversetotalshoulderarthroplasty.htm, (last modified Mar. 30, 2006), 1 pg.
Frankle, Mark, et al., "The Reverse Shoulder Prosthesis for Glenohumeral Arthritis Associated with Severe Rotator Cuff Deficiency", Journal of Bone and Joint Surgery, Inc, (2005), 1697-1705.
Harman, et al., "Initial Glenoid Component Fixation in "Reverse" Total Shoulder Arthroplasty: A Biomechanical Evaluation", In press JSES, (2005), 22 pgs.
Schmidt, Andrew H, "Shoulder Arthroplasty", Article from Medscape Today, (accessed Feb. 28, 2007), 4 pgs.
"Japanese Application Serial No. 2008-551524, Office Action mailed Mar. 5, 2013", w/English translation, 9 pgs.
"U.S. Appl. No. 12/777,862, Corrected Notice of Allowance mailed Nov. 21, 2014", 2 pgs.
"U.S. Appl. No. 12/777,862, Final Office Action mailed Jun. 9, 2014", 20 pgs.
"U.S. Appl. No. 12/777,862, Non Final Office Action mailed Dec. 20, 2013", 12 pgs.
"U.S. Appl. No. 12/777,862, Notice of Allowance mailed Sep. 15, 2014", 9 pgs.
"U.S. Appl. No. 12/777,862, Response filed Mar. 20, 2014 to Non-Final Office Action mailed Dec. 20, 2013", 12 pgs.
"U.S. Appl. No. 12/777,862, Response filed Aug. 8, 2014 to Final Office Action mailed Jun. 9, 2014", 13 pgs.
"European Application Serial No. 13184165.2, Extended European Search Report mailed Aug. 8, 2014", 7 pgs.
"Japanese Application Serial No. 2008-551524, Response filed Jun. 5, 2013 to Office Action mailed Mar. 5, 2013", (W/ English Translation), 16 pgs.
"Canadian Application Serial No. 2,868,764, Office Action mailed Jul. 14, 2015", 4 pgs.

\* cited by examiner

FIG_1

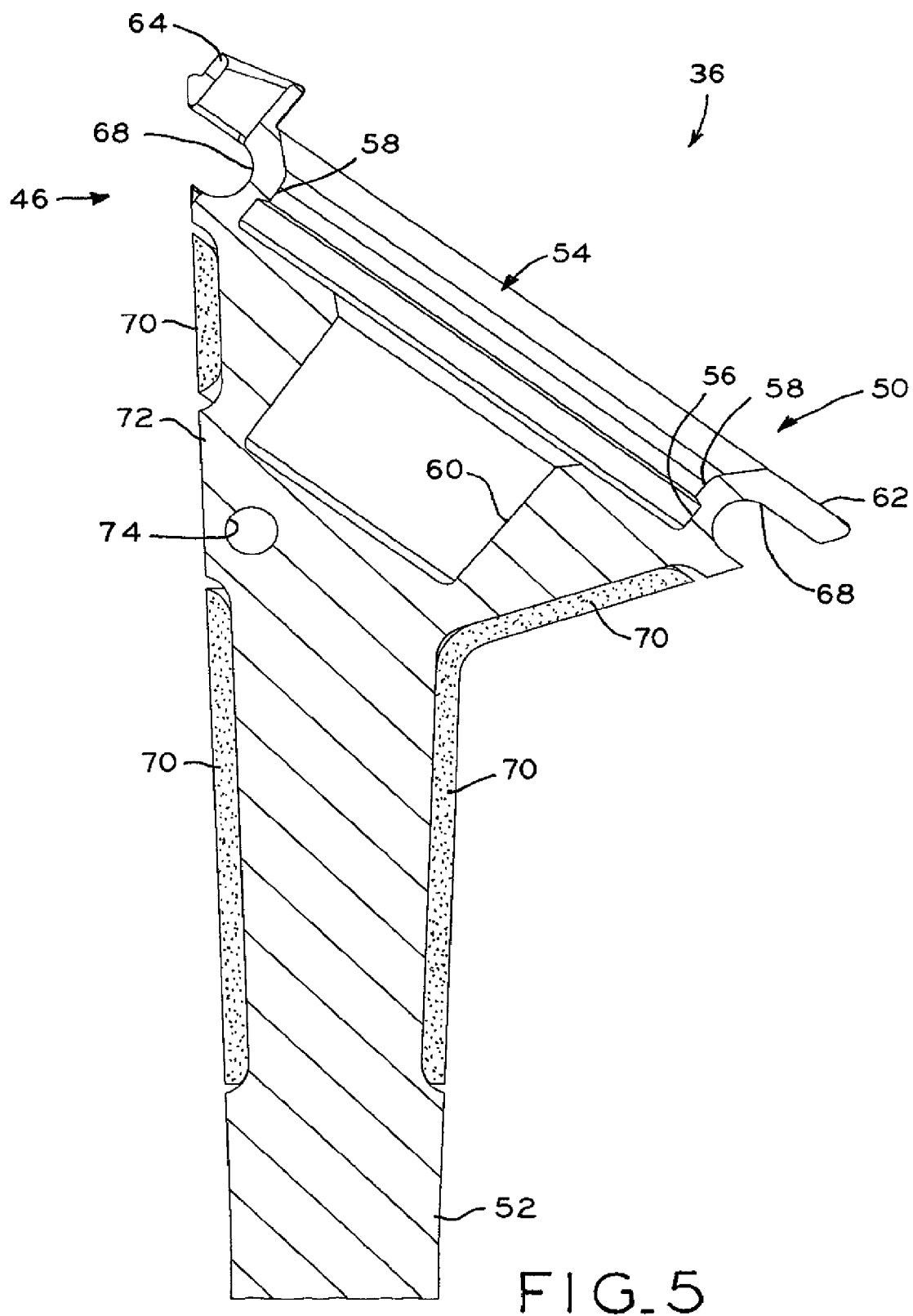
FIG._5

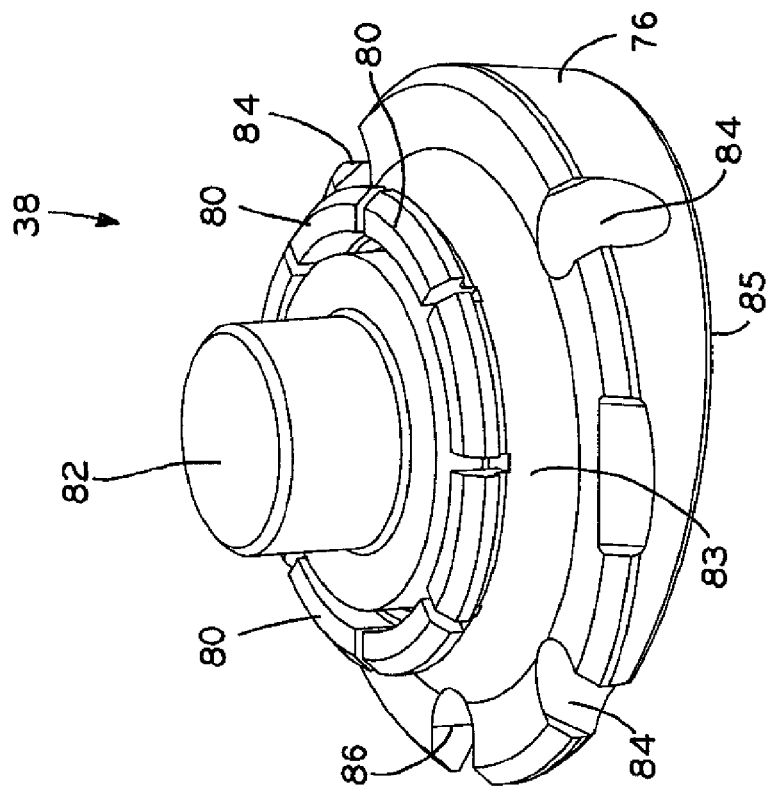
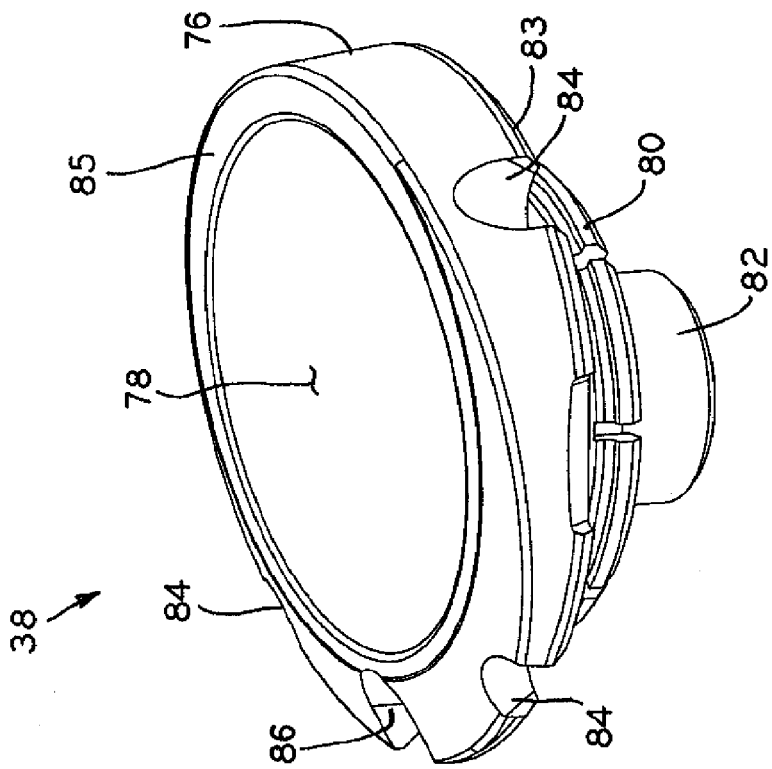

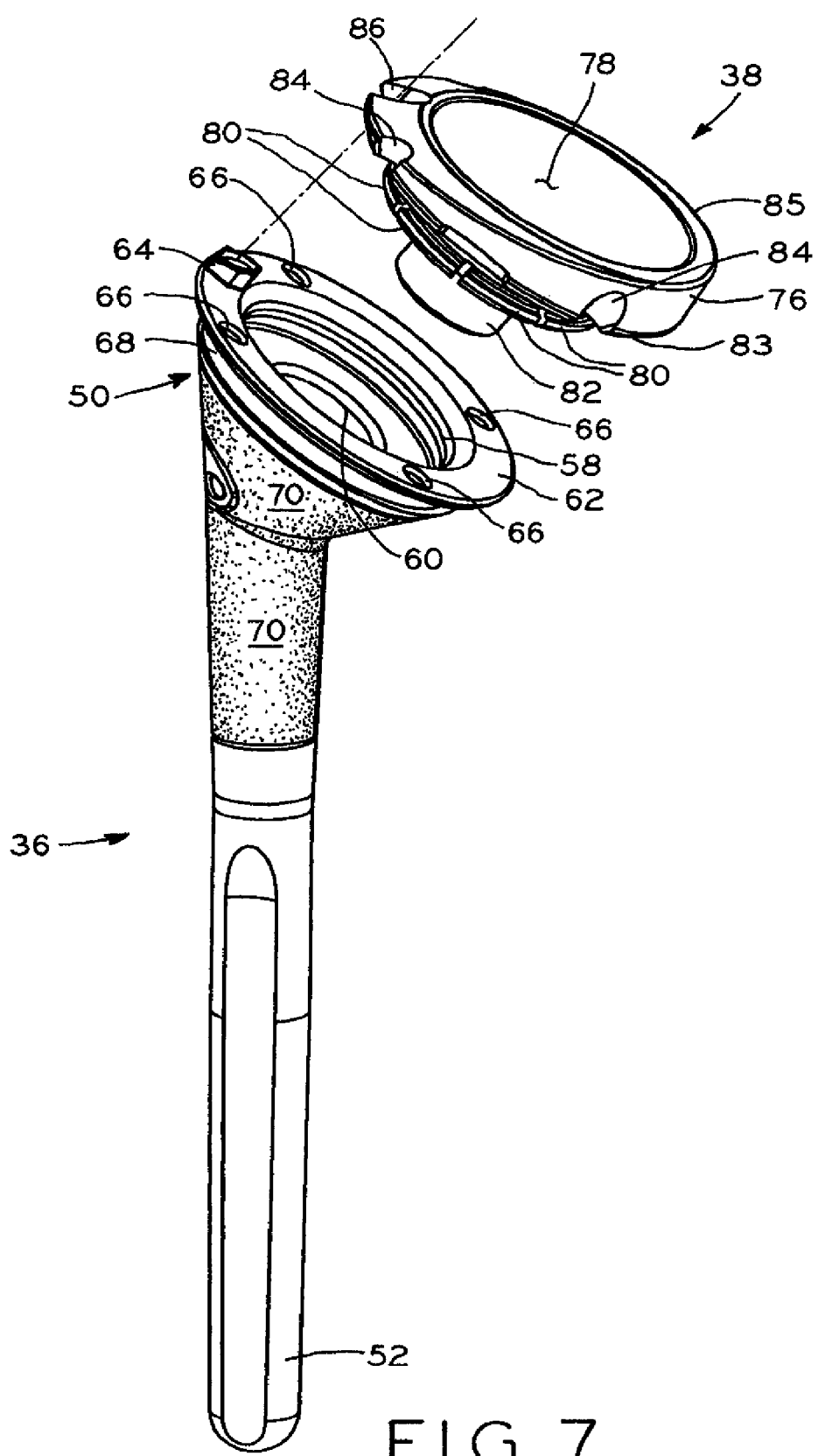
FIG_7

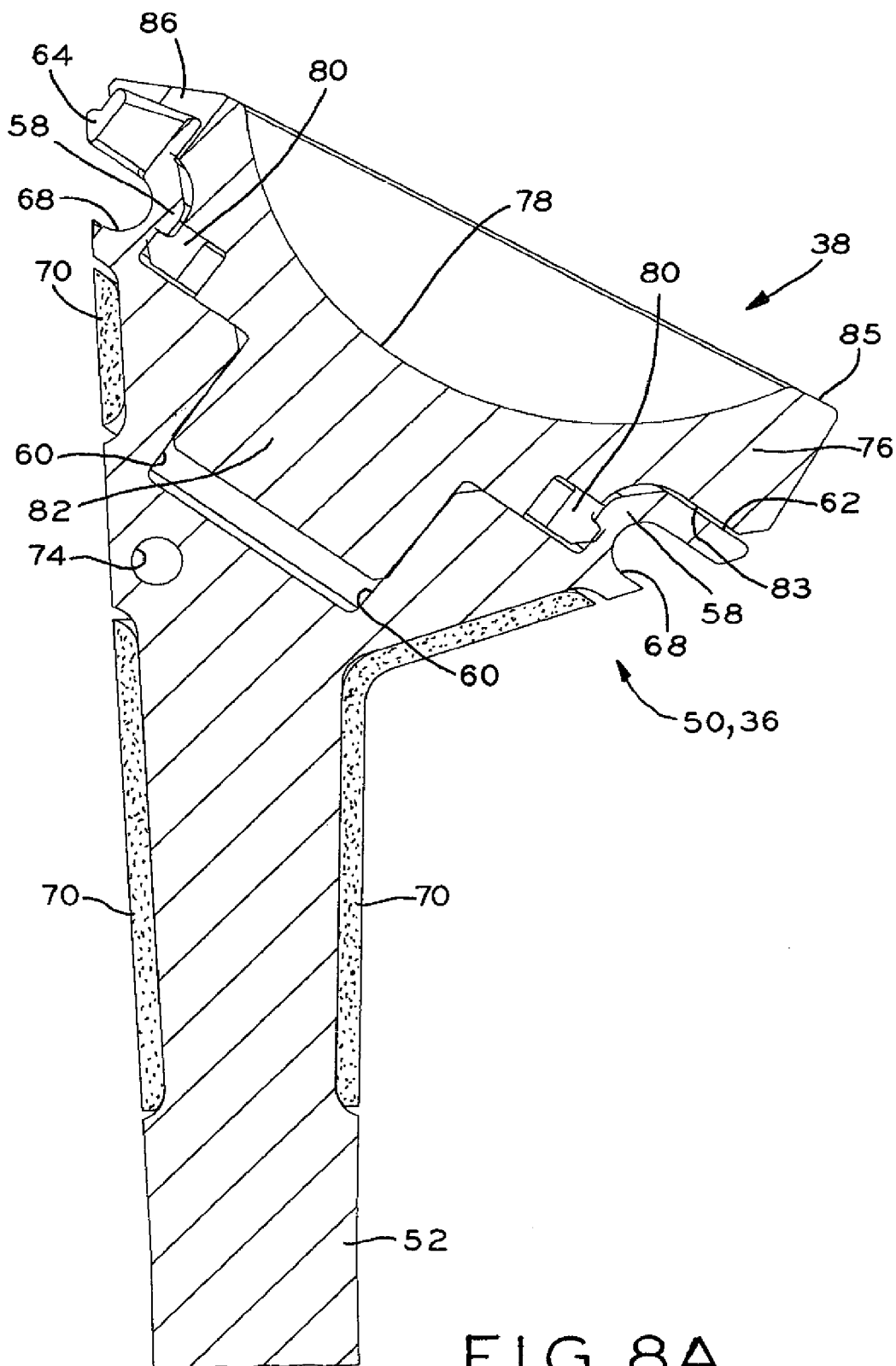
FIG_8A

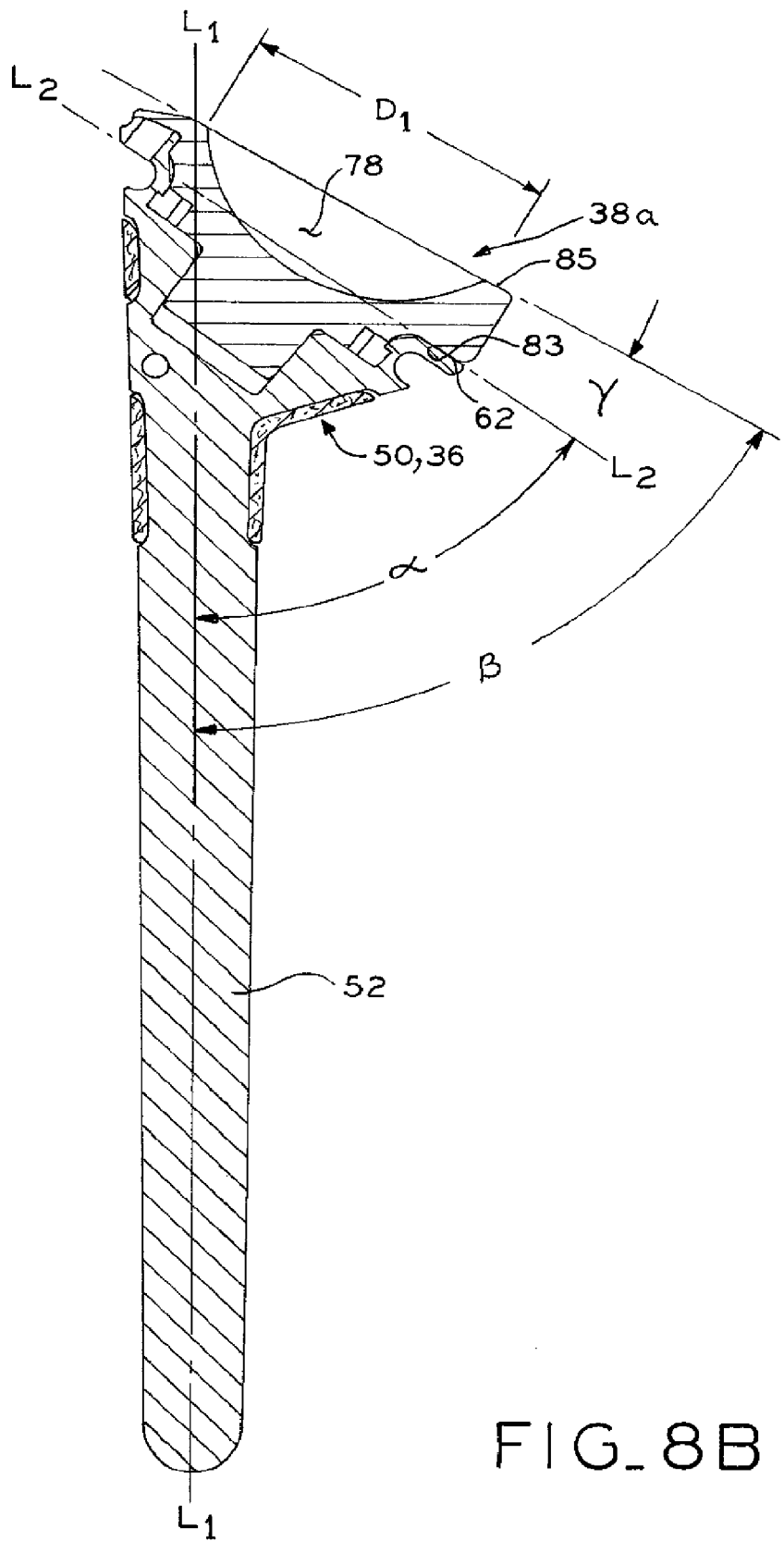
FIG_8B

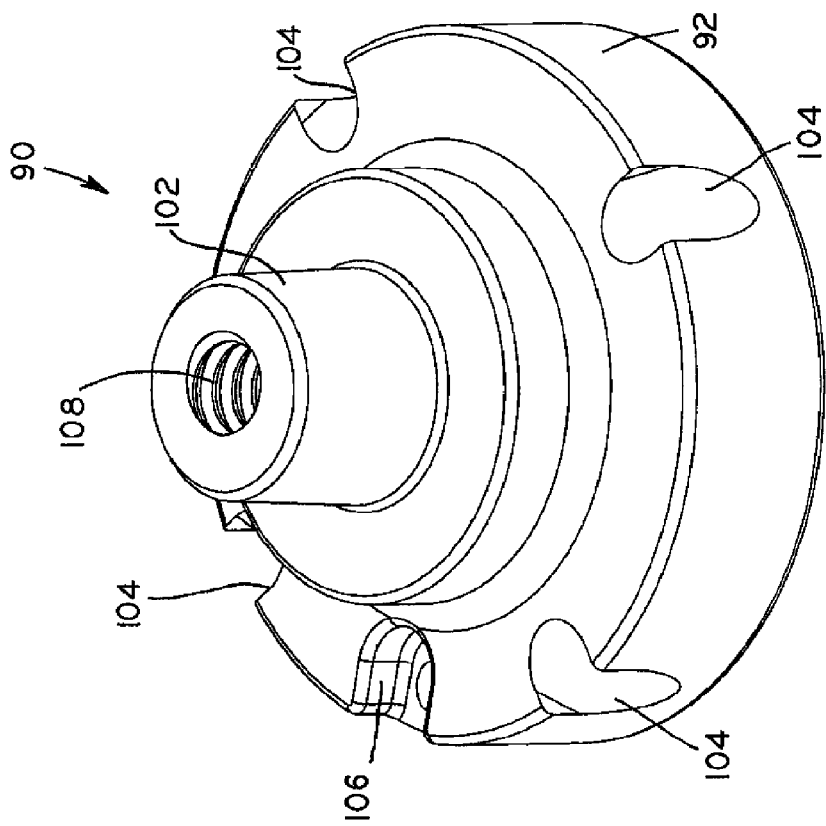
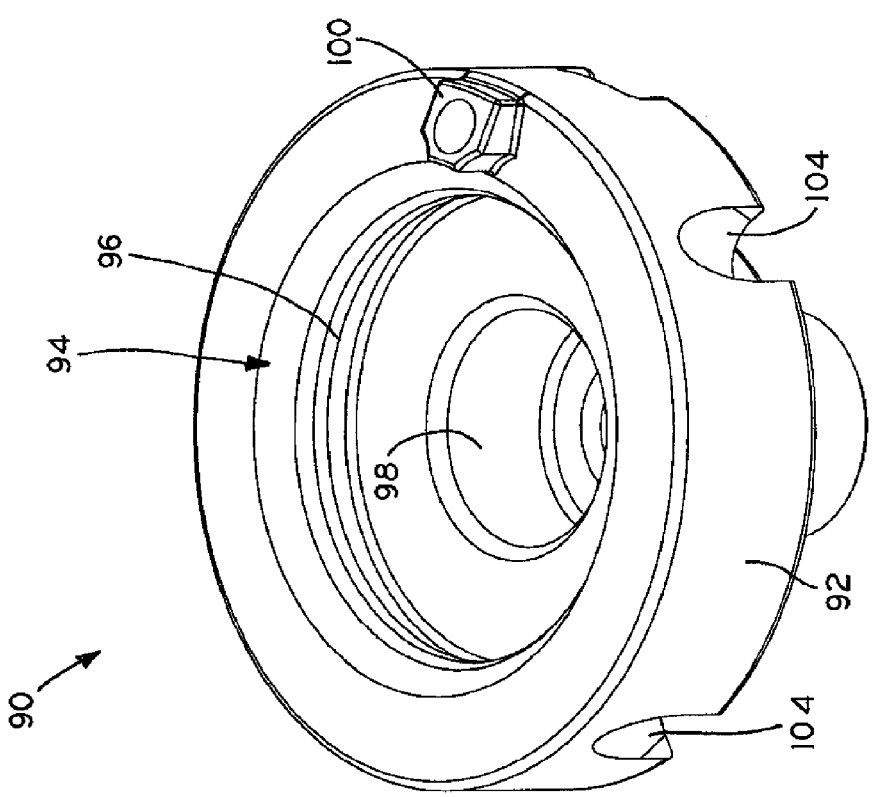

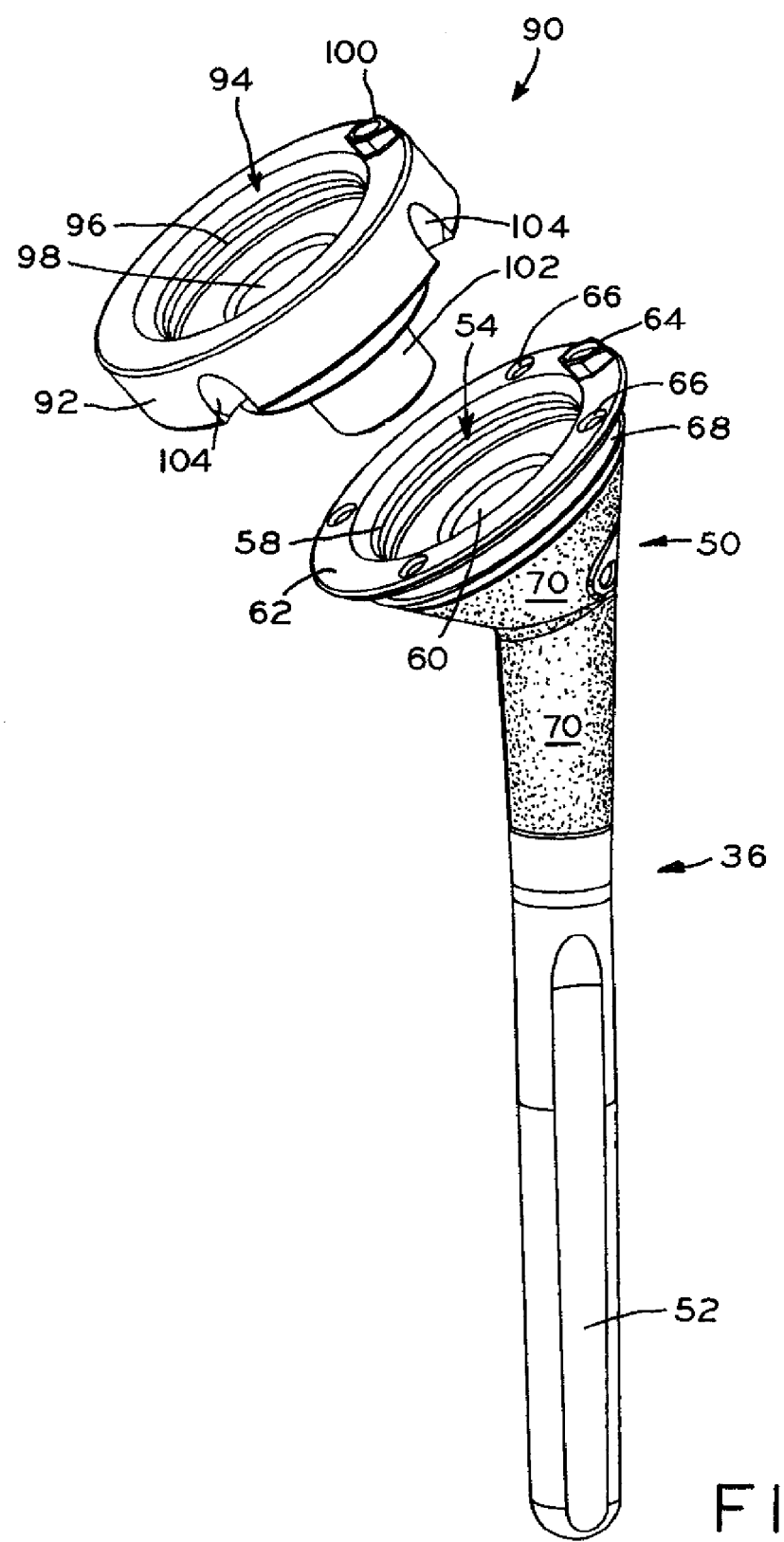
FIG_10

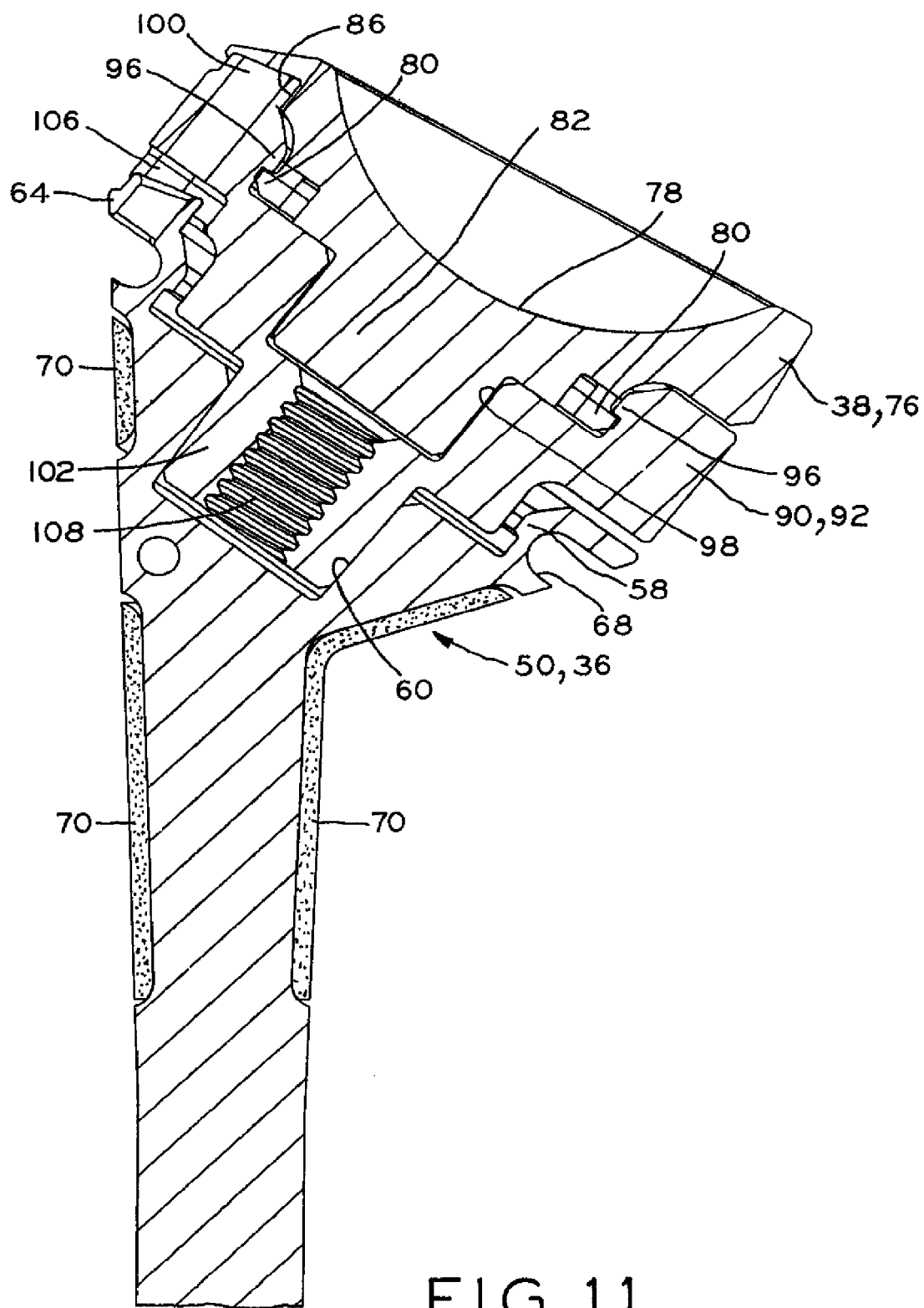
FIG_11

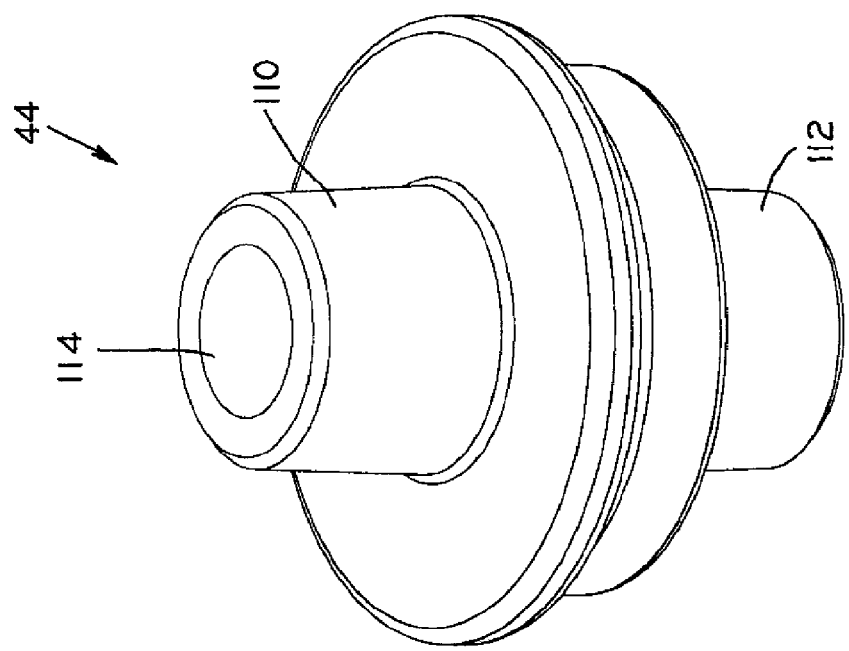
FIG._12B
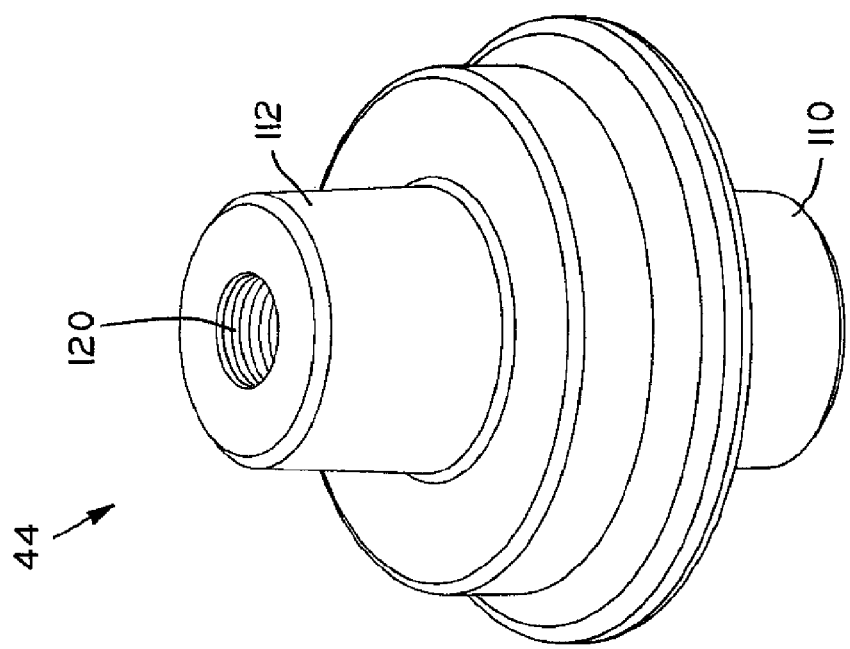
FIG._12A

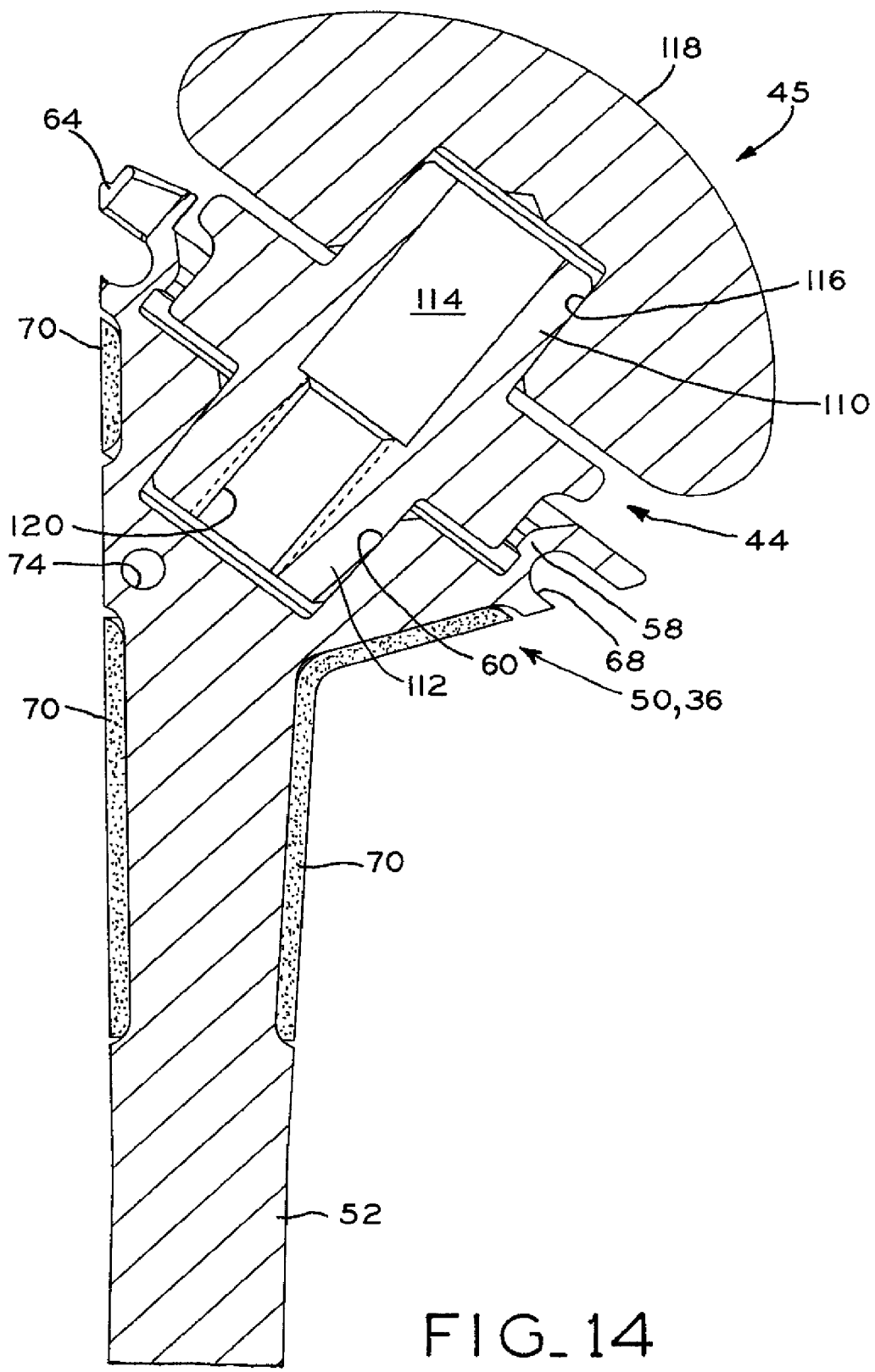
FIG_14

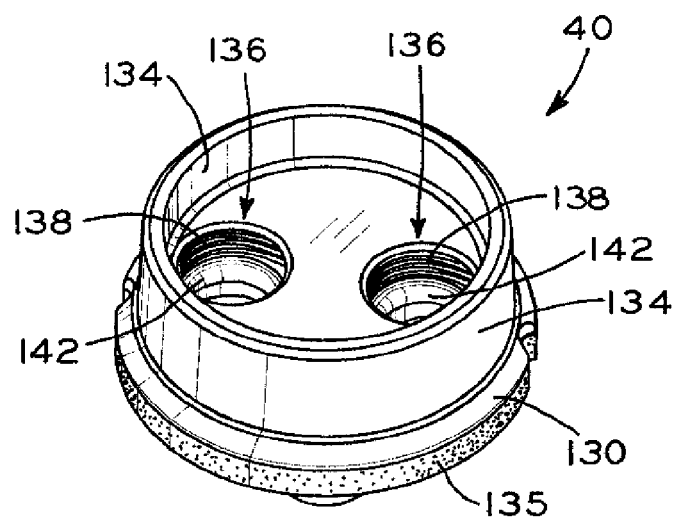
FIG_15
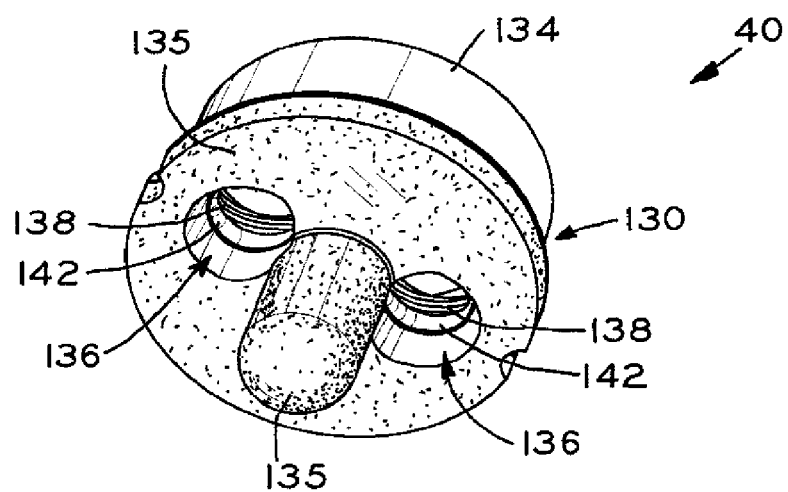
FIG_16

SHOULDER ARTHROPLASTY SYSTEM

CROSS-REFERENCE TO RELATED APPLICATION

This application is a continuation of U.S. patent application Ser. No. 12/777,862, entitled SHOULDER ARTHROPLASTY SYSTEM, filed on May 11, 2010, now issued as U.S. Pat. No. 8,940,054, which is a divisional of U.S. patent application Ser. No. 11/624,342, entitled SHOULDER ARTHROPLASTY SYSTEM, filed on Jan. 18, 2007, now issued as U.S. Pat. No. 7,854,768, which claims the benefit under Title 35, U.S.C. §119(e) of U.S. Provisional Patent Application Ser. No. 60/760,897, entitled SHOULDER ARTHROPLASTY SYSTEM, filed on Jan. 20, 2006 and U.S. Provisional Patent Application Ser. No. 60/805,012, filed on Jun. 16, 2006, entitled SHOULDER ARTHROPLASTY SYSTEM, the entire disclosures of which are expressly incorporated by reference herein.

BACKGROUND OF THE INVENTION

1. Field of the Invention

The present invention relates to surgical implant systems, including implants, instruments, and methods for performing a total shoulder arthroplasty, a hemi shoulder arthroplasty, or a "reverse" total shoulder arthroplasty.

2. Description of the Related Art

In a healthy shoulder, the proximal humerus is generally ball-shaped, and articulates within a socket formed by the scapula, called the glenoid, to form the shoulder joint. Conventional implant systems for the total replacement of the shoulder joint due to disease or trauma, i.e., a total shoulder arthroplasty, generally replicate the natural anatomy of the shoulder, and typically include a humeral component having a stem which fits within the humeral canal, and an articulating head which articulates within the socket of a glenoid component implanted within the glenoid of the scapula. An implant system for the replacement of only the humeral component of the shoulder joint, i.e., a hemi shoulder arthroplasty, typically includes only a humeral component which articulates within the natural glenoid socket of the scapula.

Recently, "reverse" type implant systems have been developed in which the conventional ball-and-socket configuration that replicates the natural anatomy of the shoulder is reversed, such that a concave recessed articulating component is provided at the proximal end of the humeral component that articulates against a convex portion of the glenoid component. Such reverse shoulder implant systems are thought to provide an increased range of motion for treatment of glenohumeral arthritis associated with irreparable rotator cuff damage, for example, by moving the center of rotation between the humeral component and the glenoid component to allow the deltoid muscles to exert a greater lever arm on the humerus.

SUMMARY OF THE INVENTION

The present invention provides an implant system for total shoulder arthroplasties and hemi shoulder arthroplasties, including a humeral stem having an enlarged head portion with interfaces adapted to removably receive various modular interchangeable components, such as articulating liners, spacers, and adapter inserts. The humeral stem functions as a universal platform that may be used in either conventional or "reverse" total shoulder arthroplasties, as well as hemi shoulder arthroplasties, and may remain implanted in place during a revision in which the implant system is converted between the foregoing configurations, for example. The articulating liner articulates against a glenoid component, and may be angled to change the neck angle of the humeral stem from an angle suited for a conventional total arthroplasty or a hemi arthroplasty to an angle suited for a "reverse" total arthroplasty. The spacer may optionally be used to fit between the humeral stem and the articulating liner to provide increased joint tension when needed. The adapter insert is used to provide an interface with a convex articulating component in a hemi arthroplasty application. A glenoid component is also provided which is mountable to the glenoid by a plurality of polyaxial locking screws, and which receives a glenosphere having a smooth, convex and uninterrupted articulating surface against which the articulating liner of the humeral component may articulate.

In one form thereof, the present invention provides a humeral implant component for use in a total shoulder arthroplasty or a hemi shoulder arthroplasty, including a stem portion extending toward a distal end thereof; a head portion at a proximal end thereof, the head portion including an internal cavity having first engagement structure and a first tapered bore; and a second component received within the internal cavity and including a first stem received within the first tapered bore.

In another form thereof, the present invention provides a humeral implant component for use in a total shoulder arthroplasty or a hemi shoulder arthroplasty, including a stem portion defining a longitudinal axis; and a head portion having first engagement structure, and a portion which defines a first angle with respect to the longitudinal axis, the first angle between about 35 and about 55 degrees.

In another form thereof, the present invention provides a humeral implant component for use in a total shoulder arthroplasty or a hemi shoulder arthroplasty, comprising a stem portion defining a longitudinal axis; and a head portion having first engagement structure, and a surface which defines a first angle with respect to the longitudinal axis; and a second component separate from the stem and secured to the first engagement structure, the second component having a second surface defining a second angle between the first surface and the second surface.

In another form thereof, the present invention provides a humeral implant component for use in a total shoulder arthroplasty or a hemi shoulder arthroplasty, including a stem portion defining a longitudinal axis; and a head portion having first engagement structure; and a second component separate from the stem and secured to the first engagement structure, the second component having a surface defining one of an anteversion angle and a retroversion angle with respect to the longitudinal axis of between about 1 and about 30 degrees.

In another form thereof, the present invention provides a humeral implant component for use in a total shoulder arthroplasty or a hemi shoulder arthroplasty, including a stem portion extending toward a distal end thereof; and a substantially enlarged head portion at a proximal end thereof, the head portion including a suture groove adjacent the proximal end.

In another form thereof, the present invention provides a glenoid implant component for use in a total shoulder arthroplasty, including a body having a stem extending from a medial side thereof; at least one hole in the body including a substantially convex seat therein; at least one screw extendable through the hole, the screw including a threaded shank and an at least partially spherical head, the head abuttable against the seat; and a screw retainer movable between a first position wherein the screw head may move polyaxially with respect to the seat and a second position wherein the screw head is retained in a fixed position with respect to the seat.

In another form thereof, the present invention provides a glenoid implant component for use in a total shoulder arthroplasty, including a base member, including a substantially cup-shaped body having a base wall; and a tapered annular wall extending from a lateral side of the base wall; and an articulating component, including a medial side including a tapered bore receivable onto the tapered annular wall of the base member; and a lateral side defining a substantially smooth, uninterrupted, convex articulating surface.

In another form thereof, the present invention provides a glenoid component of a reverse shoulder system for implanting on the glenoid of a shoulder, the glenoid component including a glenoid base including a bone engaging first surface and an opposing second surface, the glenoid base including at least one fastener receiving hole extending through the glenoid base from the first surface to the second surface, each fastener receiving hole including a threaded portion proximal the second surface and a substantially spherical portion adjacent the threaded portion and proximal the first surface relative to the threaded portion, the glenoid base having an annular wall extending outwardly from the second surface; a glenosphere having an articulating surface and defining a bore, the annular wall of the glenoid base received within the bore to couple the glenosphere to the glenoid base; a screw having a head and a threaded shank and extending through the at least one fastener receiving hole and insertable into the glenoid, the head being at least partially spherical in shape and configured to be retained in the spherical portion of the at least one fastener receiving hole; and a locking member threadedly engaged with the threaded portion of the fastener receiving hole and abutting the head of the fastener to secure the head of the fastener in the fastener receiving hole.

In another form thereof, the present invention provides a glenoid component of a shoulder prosthesis system for implanting on the glenoid of a shoulder, the glenoid component including a glenoid base including a bone engaging first surface and an opposing second surface, the glenoid base including at least one fastener receiving hole extending through the glenoid base from the first surface to the second surface, each fastener receiving hole including a threaded portion proximal the second surface and a substantially spherical portion adjacent the threaded portion and proximal the first surface relative to the threaded portion; a screw having a head and a threaded shank extending through the at least one fastener receiving hole and insertable into the glenoid, the head being at least partially spherical in shape and configured to be retained in the spherical portion of the at least one fastener receiving hole; and a locking member threadedly engaged with the threaded portion of the fastener receiving hole, the locking member abutting the head of the screw and restricting movement of the head within the spherical portion of the fastener receiving hole.

In another form thereof, the present invention provides a reverse shoulder prosthesis system for the repair or replacement of a shoulder joint, the shoulder joint including a humerus and a scapula, the reverse shoulder prosthesis system including a ball assembly mountable on the scapula, the ball assembly including a glenoid base including a bone engaging first surface and an opposing second surface, the glenoid base including at least one fastener receiving hole extending through the glenoid base from the first surface to the second surface, each fastener receiving hole including a threaded portion proximal the second surface and a substantially spherical portion adjacent the threaded portion and proximal the first surface relative to the threaded portion; a glenosphere having an articulating surface and removably mounted to the base proximal the second surface; a screw having a head and a threaded shank extending through the at least one fastener receiving hole and insertable into the scapula, the head being at least partially spherical in shape and configured to be retained in the spherical portion of the at least one fastener receiving hole; and a locking member threadedly engaged with the threaded portion of the fastener receiving hole, the locking member abutting the head of the fastener and restricting movement of the head within the spherical portion of the fastener receiving hole.

In another form thereof, the present invention provides a glenoid implant component for use in a total shoulder arthroplasty, including a glenoid base including a bone engaging first surface and an opposing second surface, the glenoid base having first engagement structure extending from the second surface; a glenosphere having an articulating surface and second engagement structure configured to engage the first engagement structure; and polyaxial means for anchoring the glenoid component to a glenoid.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 5 is a sectional view through a medial/lateral plane, showing the proximal end of the humeral stem;

FIG. 6A is a perspective view of the proximal end of an articulating liner;

FIG. 6B is a perspective view of the distal end of the articulating liner of FIG. 6A;

FIG. 7 is an exploded view of the humeral stem and articulating liner;

FIG. 8A is a partial sectional view through a medial/lateral plane, showing the connection between the humeral stem and an articulating liner;

FIG. 8B is a partial sectional view through a medial/lateral plane, showing the connection between the humeral stem and the articulating liner of FIG. 7;

FIG. 9A is a perspective view of the proximal end of a spacer;

FIG. 9B is a perspective view of the distal end of the spacer of FIG. 9A;

FIG. 10 is an exploded view of the humeral stem and a spacer;

FIG. 11 is a partial sectional view through a medial/lateral plane, showing the connection between the humeral stem and the spacer of FIG. 10, and further showing the connection between the spacer and an articulating liner;

FIG. 12A is a perspective view of the distal end of an adapter insert;

FIG. 12B is a perspective view of the proximal end of the adapter insert of FIG. 12B;

FIG. 14 is a partial sectional view through a medial/lateral plane, showing the connection between the humeral stem, adapter insert, and humeral head of FIG. 13;

FIG. 15 is a perspective view of the lateral side of a glenoid base;

FIG. 16 is a perspective view of the medial side of the glenoid base;

Corresponding reference characters indicate corresponding parts throughout the several views. The exemplifications set out herein illustrate exemplary embodiments of the invention, and such exemplifications are not to be construed as limiting the scope of the invention any manner.

DETAILED DESCRIPTION

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves.

Figure 1:
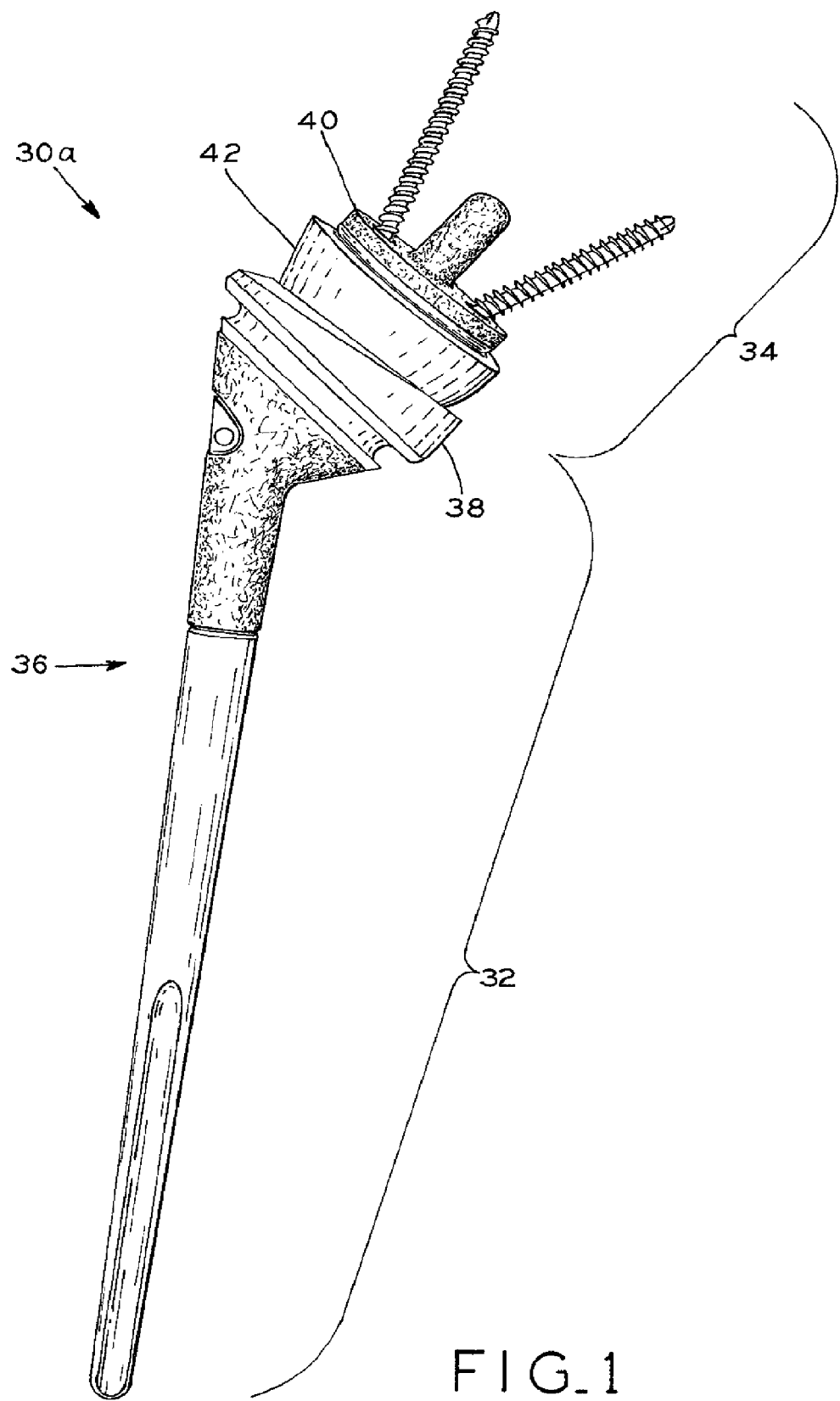
FIG. 1 is a perspective view of a "reverse" total shoulder arthroplasty implant system according to the present invention, including a humeral component and a glenoid component.

Referring to FIG. 1, implant system 30a for a "reverse" total shoulder arthroplasty is shown, which generally includes a humeral component 32 adapted to be fitted within a prepared proximal end and canal of a humerus, and a glenoid component 34 mounted to a prepared surface of the glenoid via a plurality of screws, wherein the humeral component 32 articulates about the glenoid component 34 to replicate the movement of the natural shoulder joint. As described in further detail below, humeral component 32 generally includes humeral stem 36 and articulating liner 38 fitted to humeral stem 36 and having a convex articulating surface, and glenoid component 34 generally includes a glenoid base 40 and a glenosphere 42 fitted to glenoid base 40 and having a convex articulating surface, wherein articulating liner 38 articulates about glenosphere 42.

Figure 2:
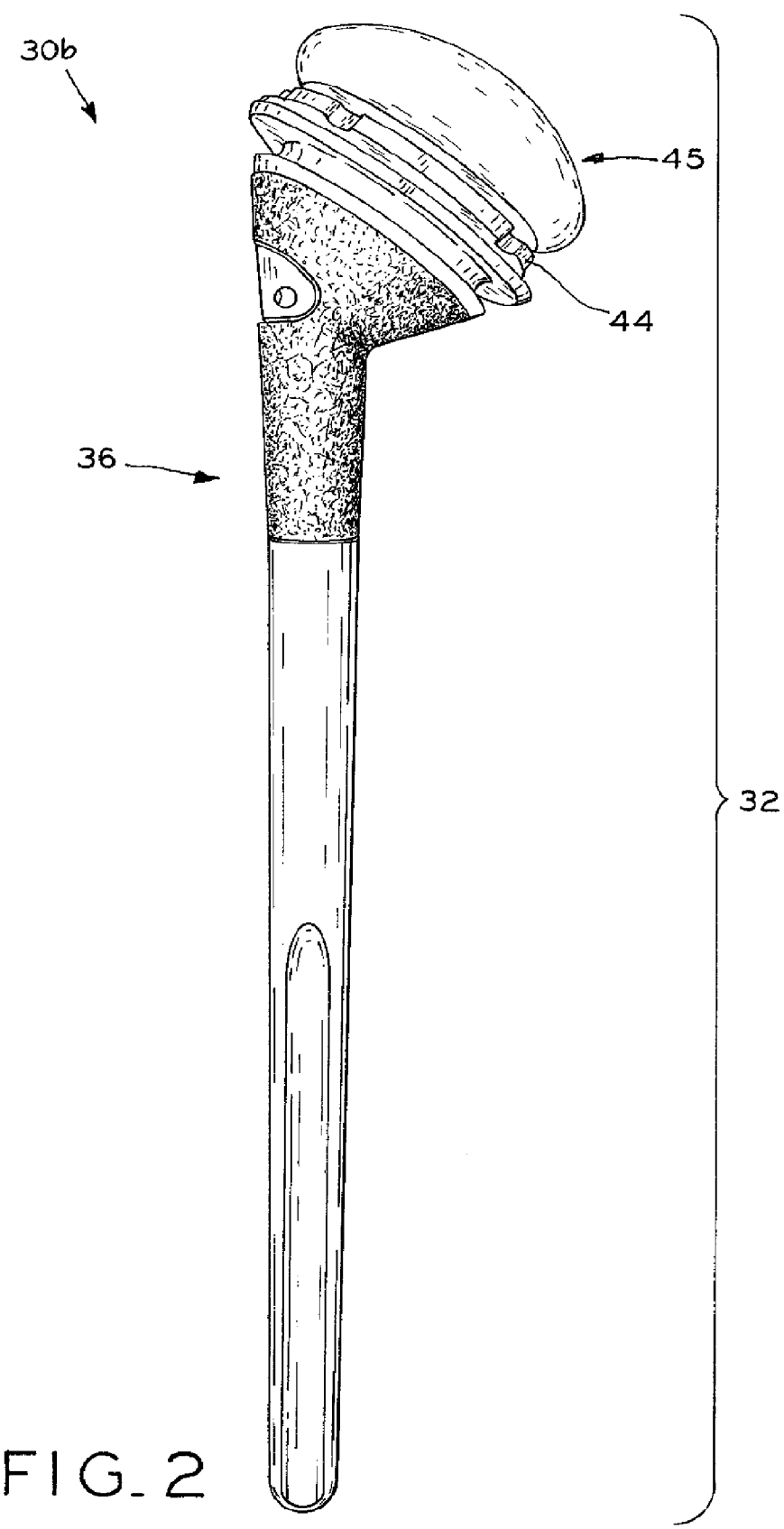
FIG. 2 is a perspective view of the humeral component of a conventional total shoulder arthroplasty implant system or a hemi shoulder arthroplasty system.

Referring to FIG. 2, implant system 30b for a conventional total shoulder arthroplasty or a hemi shoulder arthroplasty is shown, which generally includes humeral component 32 that articulates against a conventional glenoid component (not shown) in a conventional total shoulder arthroplasty or which articulates against the intact glenoid of the scapula in a hemi shoulder arthroplasty. Humeral component 32 generally includes humeral stem 36, an adapter insert 44, and a humeral head 45 fitted to adapter insert 44 and having a convex articulating surface.

Figure 3:
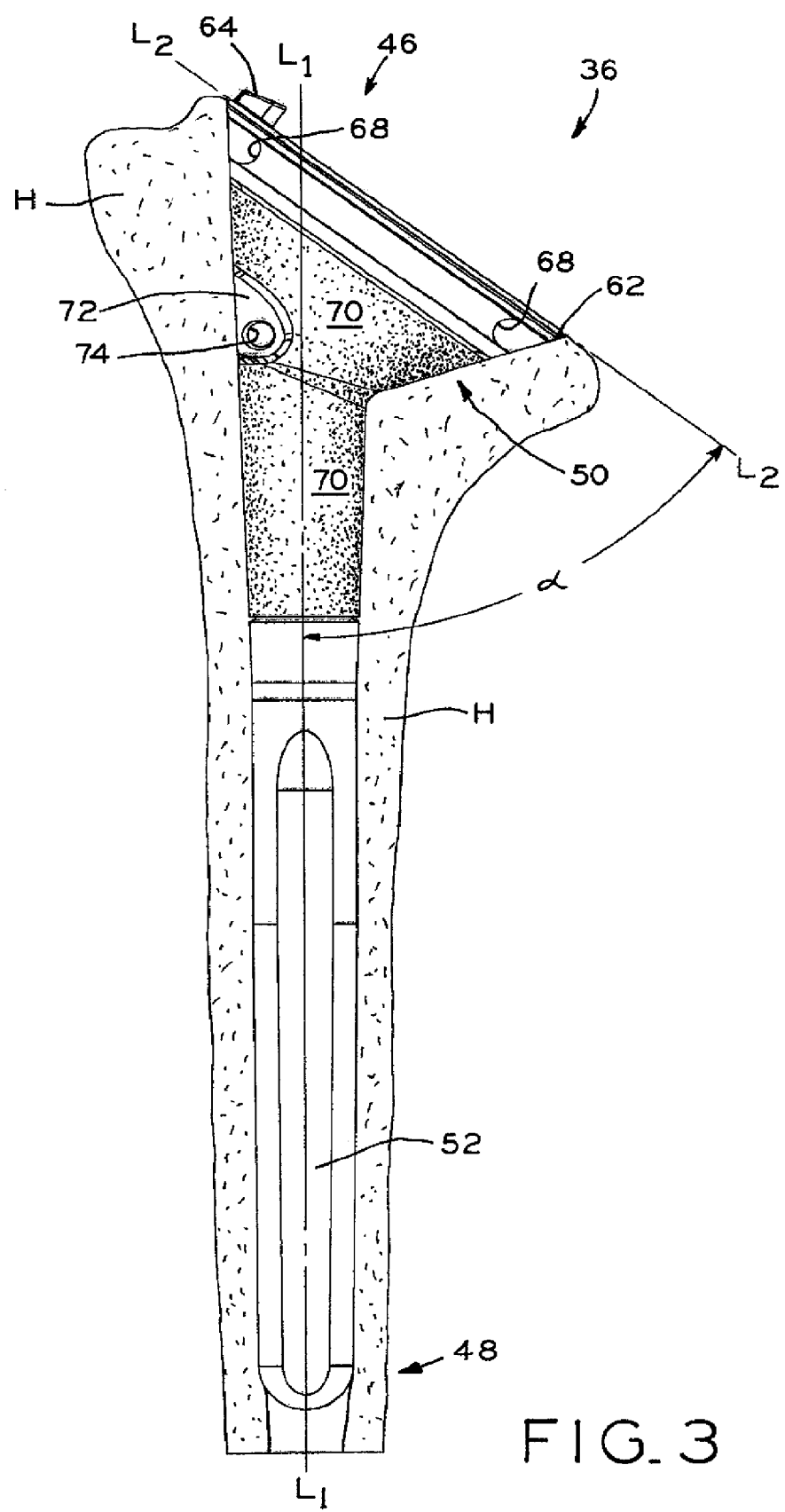
FIG. 3 is a side view of the humeral stem through a medial/lateral plane, further showing an outline of the humerus.
Figure 4:
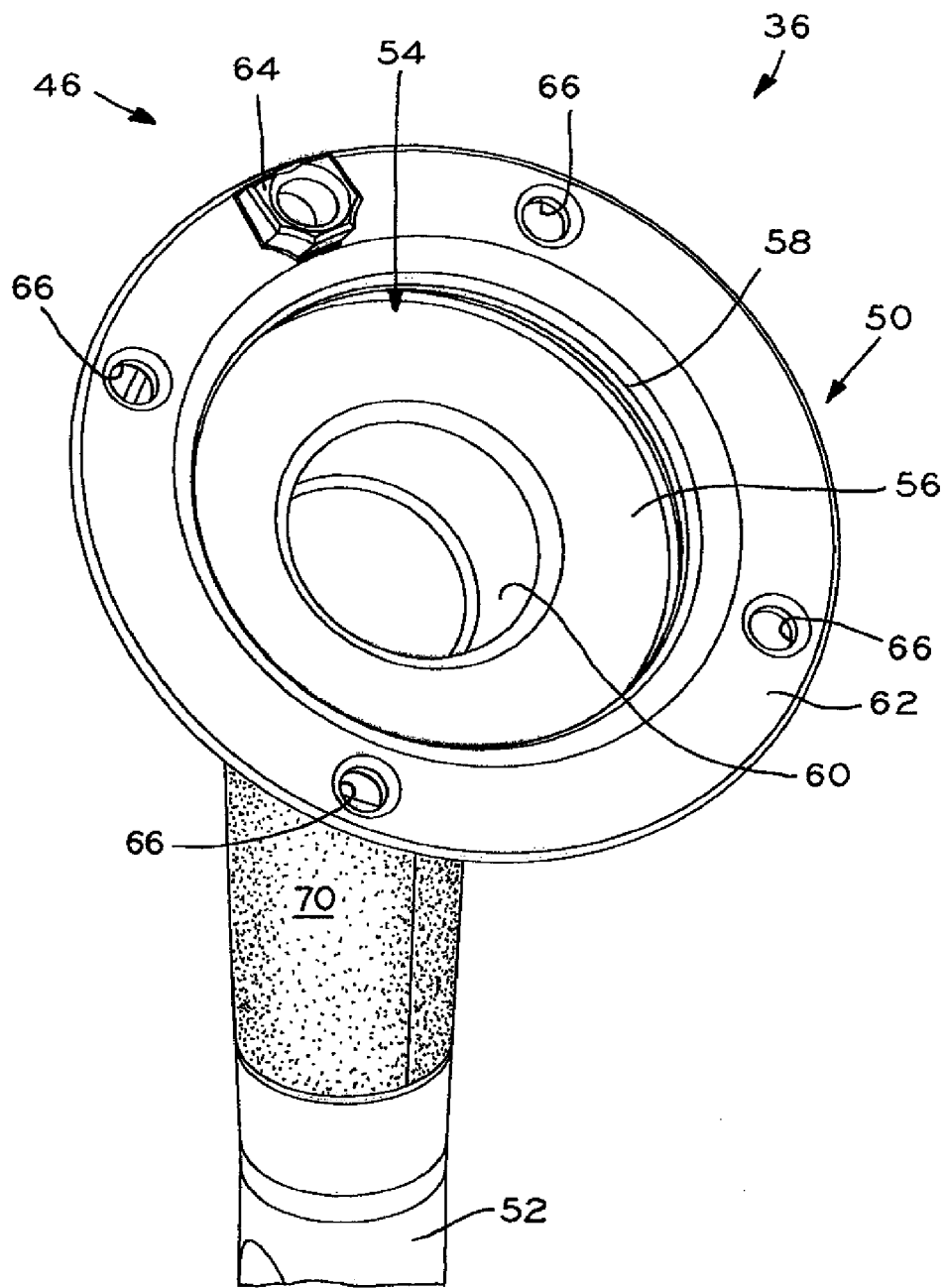
FIG. 4 is a perspective view of the proximal end of the humeral stem.

Referring to FIGS. 3-5, humeral stem 36 is shown, having proximal end 46 and distal end 48. Humeral stem 36 includes head portion 50 at proximal end 46 and stem portion 52 extending toward distal end 48. In the embodiment shown is FIGS. 3-5, head portion 50 and stem portion 52 are unitarily formed as a single piece; however, head portion 50 and stem portion 52 may also be formed of separate components joined to one another. Humeral stem 36, as well as the other implant components described herein, may be made of a suitable biocompatible metal, such as titanium, for example, or from other materials as described below. Head portion 50 of humeral stem is substantially enlarged with respect to stem portion 52, and flares outwardly from stem portion 52 in shape towards proximal end 46 of humeral stem 36. As may be seen from FIG. 3, after the proximal end of the humerus is resected and the humeral canal and proximal humeral end are prepared using known instruments (not shown) and methods, stem portion 52 is received in the prepared canal of the humerus, and head portion 50 is received within a conically reamed portion of at the proximal end of the resected humerus.

As shown in FIGS. 4 and 5, head portion 50 includes an internal cavity 54 extending into the proximal end thereof, including a first, relatively larger diameter portion 56 with an annular rib 58 and a second, relatively smaller diameter portion defining a tapered bore 60. An annular, outer rim 62 is formed about the proximal end 46 of head portion 50 and includes an instrument seat 64 with a central bore which may be used to anchor and locate an impaction instrument (not shown) for impacting humeral stem 36 into a reamed and prepared canal in the humerus. A plurality of suture holes 66 are defined in outer rim 62 and, as shown in FIGS. 3 and 5, a suture groove 68 is disposed beneath and adjacent outer rim 62, the functions of which will be described below.

Humeral stem 36 additionally includes, toward the proximal end 46 thereof, a plurality of recessed portions, best seen in FIG. 5, in which are disposed pads or coating portions 70 of a highly porous biomaterial useful as a bone substitute and/or cell and tissue receptive material for promotion of bone ingrowth to aid in the osseointegration of humeral stem 36 within the humerus. An example of such a material is produced using Trabecular Metal™ technology available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is incorporated herein by reference. As would be apparent to one skilled in the art, although the embodiments described herein utilize porous tantalum, other metals such as niobium, or alloys of tantalum and niobium with one another or with other metals may also be used.

Referring to FIGS. 3 and 5, head portion 50 of humeral stem 36 additionally includes a hub section 72 of titanium on a lateral side thereof having a suture hole 74 through which sutures may be threaded to aid in reducing humeral fractures as needed. Suture holes 66 and suture groove 68 of head portion 50 of humeral stem 36 may also be used by a surgeon to reconstruct the proximal humerus in the event of humeral fractures, or for the attachment of soft tissue. For example, one or more of suture holes 66 may be used to anchor sutures wrapped around bone fragments of the upper humerus using suture groove 68, for example, to bring the lesser and greater tuberosities into reduction circumferentially about humeral stem 36, or to attach soft tissue circumferentially about humeral stem 36. Also, a surgeon may selectively use one, two, three or all of suture holes 66 alone or in combination with each other and with suture groove 68 as needed for this purpose. Additionally, the axial clearance beneath outer rim 62 of humeral stem 36 provided by suture groove 68 allows the surgeon to use one or more of suture holes 66 for "pull down" sutures to pull bone fragments along the axial direction of humeral stem 36 for reduction of fractures or for attachment of soft tissue, for example.

Referring to FIG. 3, outer rim 62 at the proximal end of head portion 50 of humeral stem 36 defines a substantially flat or planar surface which, as shown, is disposed substantially along a resection cut line $L_2$-$L_2$ along which a surgeon makes a resection cut to resect the proximal humerus H when humeral stem 36 is implanted during a total or hemi shoulder arthroplasty. A first neck angle α is defined in a medial/lateral plane between the surface of outer rim 62 along resection cut line $L_2$-$L_2$, and the longitudinal axis $L_1$-$L_1$ of humeral stem 36. Neck angle α may be as little as about 35, 40, or 45 degrees, and may be as great as about 50 or 55 degrees when humeral stem 36 is used in a conventional shoulder arthroplasty or in a hemi arthroplasty, as described below. In the embodiment of FIG. 3 and in FIGS. 8B and 8C discussed below, neck angle α is about 53 degrees. Further, as also described below, an articulating liner may be used to provide a greater neck angle with respect to longitudinal axis $L_1$-$L_1$ of humeral stem 36 which is more suited to a "reverse" shoulder arthroplasty.

Referring to FIGS. 6A and 6B, proximal and distal perspective views respectively, of an articulating liner 38 for fitting to humeral stem 36 are shown, including a body 76 which may be formed of a single, integral piece of ultra high molecular weight polyethylene ("UHMWPE"), for example. The proximal end of articulating liner 38 includes a convex articulating surface 78 for articulating against glenosphere 42 (FIG. 1) of glenoid component 34. The distal end of articulating liner 38 includes a plurality of spring fingers 80 spaced therearound and a post 82 which may be non-tapered to provide an interference fit within tapered bore 60 of humeral stem 36. Articulating liner 38 further includes a plurality of recesses 84 disposed about the outer periphery of body 76 for providing clearance for accessing suture holes 66 of humeral stem 36 when articulating liner 38 is attached to humeral stem 36 in the manner described below.

Referring additionally to FIGS. 7 and 8, articulating liner 38 is attachable to humeral stem 36 by using an impaction instrument (not shown) which may include a first portion fitting within the cavity defined by articulating surface 78 and a second, prong-type portion insertable through notch 86 in the outer periphery of body 76 of articulating liner 38 and through the bore of instrument seat 64 of humeral stem 36 to rotationally locate articulating liner 38 with respect to humeral stem 36, with post 82 of articulating liner 38 received within tapered bore 60 of humeral stem 36 by an interference fit. Thereafter, articulating liner 38 is impacted into internal cavity 54 of humeral stem 36 until spring fingers 80 of articulating liner 38 resiliently engage behind annular rib 58 of humeral stem 36 to thereby axially lock articulating liner 38 with respect to humeral stem 36, with rotation of articulating liner 38 with respect to humeral stem 36 prevented by the engagement of instrument seat 64 of humeral stem 36 within notch 86 of articulating liner 38.

Figure 8C:
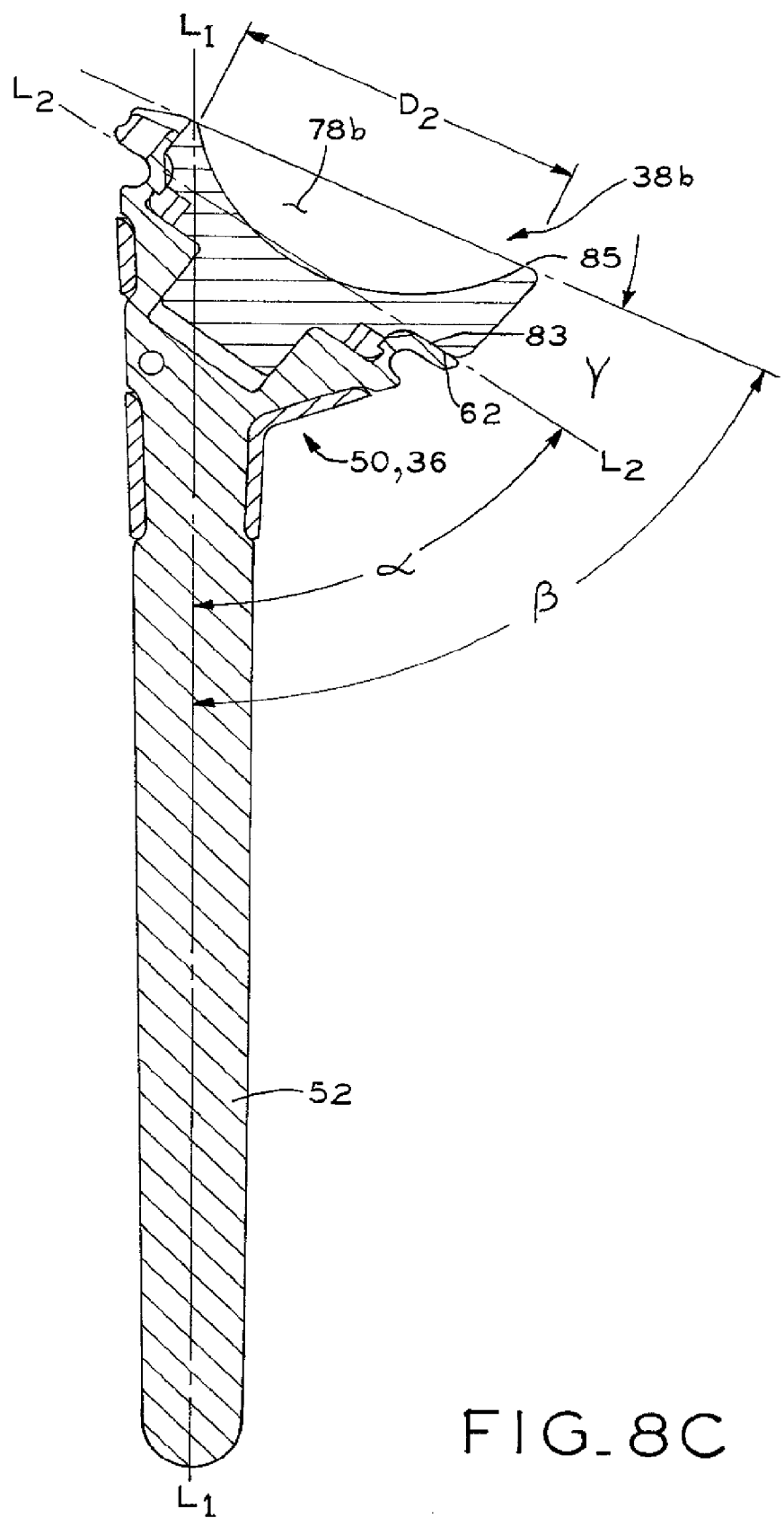
FIG. 8C is a partial sectional view through a medial/lateral plane, showing the connection between the humeral stem and a second articulating liner.

As shown in FIGS. 6A-8C, articulating liner 38 is substantially wedge-shaped, having an annular lower surface 83 in abutment with outer rim 62 of head portion 50 of humeral stem 36 as shown in FIGS. 8B and 8C, and an annular upper surface 85 opposite lower surface 83. As shown in FIGS. 8B and 8C, lower and upper surfaces 83 and 85 together define an angle γ therebetween in a medial/lateral plane which may be as small as about 1 or 5 degrees, or may be as large as about 15, 30, or 35 degrees, or may be sized at any one degree increment therebetween, for example. In the embodiment of FIG. 8B, a first articulating liner 38a defines an angle γ of about 7 degrees and, in the embodiment of FIG. 8C, a second articulating liner 38b defines an angle γ of about 12 degrees. Further details of first and second articulating liners 38a and 38b are discussed below. When an articulating liner 38a or 38b is secured to head portion 50 of humeral stem 36 in the manner described above, the upper surface 85 of the articulating liner defines a second neck angle β with respect to longitudinal axis $L_1$-$L_1$ of humeral stem 36 or, stated another way, the first neck angle α, between longitudinal axis $L_1$-$L_1$ of humeral stem 36 and outer rim 62 along resection cut line $L_2$-$L_2$, and the angle γ of articulating liner 38 combine to define second neck angle β. As with first neck angle α and angle γ of articulating liner 38, second neck angle β is in a medial/lateral plane. Second neck angle β may be as small as about 55 or 60 degrees, or may be as large as about 65 or 70 degrees when humeral stem 36 is configured for a "reverse" shoulder arthroplasty, and the articulating liner 38 may be selected from a plurality of articulating liners 38 having varying angle γ to provide proper stability for the shoulder joint. In the embodiment of FIG. 8B, second neck angle β is about 60 degrees and in the embodiment of FIG. 8C second neck angle β is about 65 degrees.

Articulating liner 38 may be selected by a surgeon from a plurality of differently-sized articulating liners, having varying size diameters and heights, for example, to provide a properly sized articulating liner for a given patient anatomy and/or joint reconstruction need. Additionally, a plurality of trial or provisional articulating liners (not shown) may be provided with the present implant system, which lack spring fingers 80 and/or post 82 but otherwise are substantially identical to the implanted articulating liner 38. In this manner, a surgeon may use such provisional articulating liners during the arthroplasty procedure to determine the correct size of articulating liner to be implanted, followed by selecting the desired articulating liner and securing same to humeral stem 36 in the manner described above.

Referring to FIGS. 8B and 8C, two differently-sized articulating liners 38a and 38b are shown, which are structurally identical except for the diameter of articulating surfaces 78a and 78b thereof. In one embodiment, articulating liner 38a has an articulating surface 78a with a diameter $D_1$ of 36 mm, and articulating liner 38b has an articulating surface 78b with a diameter $D_2$ of 40 mm. However, the diameters of the articulating liners 38 may be as small as about 30 mm, 32 mm, or 34 mm, or may be as large about 50 mm, 55 mm, or 60 mm, or may be sized at any one degree increment therebetween, for example. Articulating liner 38a may typically be used in most patients; however, articulating liner 38b may be used in relatively larger patients, or in other cases where a greater diameter articulating surface may be desired such as, for example to provide greater joint stability. Advantageously, because the above-described structure by which articulating liners 38a and 38b are secured to head portion 50 of humeral stem 36 is identical, a surgeon may intra-operatively select an appropriate articulating liner from articulating liner 38a, articulating liner 38b, or an articulating liner having a differently sized or differently dimensioned articulating surface (not shown) based on the anatomical needs of a particular patient. Thus, a series of articulating liners may be provided, having varying articulating surface diameters or other dimensions, which are compatible with humeral stem 36.

Optionally, spacers 90 (FIGS. 9A-11) of various size, described below, may be used to provide increased tension on the shoulder joint when needed in the event that the height of articulating liner 38 is not sufficient to provide such tension. Referring to FIGS. 9A and 9B, proximal and distal perspective views, respectively, of a spacer 90 are shown, including a body 92 which may be formed of titanium, for example. The proximal end of spacer 90 includes internal cavity 94 having an annular rib 96 and a bore 98 which dimensionally replicate the internal cavity 54 of humeral stem 36 and in particular, the annular rib 58 and bore 60 of humeral stem 36, described above. Additionally, spacer 90 includes instrument seat 100 replicating instrument seat 64 of humeral stem 36, described above. The distal end of spacer 90 includes tapered stem 102 for lockably fitting within tapered bore 60 of humeral stem 36. Body 92 of spacer 90 includes a plurality of recesses 104 disposed about an outer periphery thereof for providing clearance for accessing suture holes 66 of humeral stem 36 when spacer 90 is attached to humeral stem 36 in the manner described below.

In use, referring additionally to FIGS. 10 and 11, spacer 90 may be fitted to humeral stem 36 using a suitable instrument (not shown) in substantially the same manner as articulating liner 38 described above, with tapered stem 102 of spacer 90 providing a tapered lock fit within tapered bore 60 of humeral stem 36, and with relative rotation between spacer 90 and humeral stem 36 prevented by engagement of instrument seat 64 of humeral stem 36 within notch 106 (FIG. 9B) of spacer 90 disposed opposite seat 100 of spacer 90. Thereafter, a selected articulating liner 38 may be attached within internal cavity 94 of spacer 90 in the same manner as that described above with respect to the attachment of articulating liner 38 to humeral stem 36, namely, by engaging spring fingers 80 of articulating liner 38 with annular rib 96 of spacer 90 and receipt of post 82 of articulating liner 38 within bore 98 of spacer 90. Spacer 90 also includes a threaded central bore 108 that may be used for threading receipt of a threaded end of a retrieval instrument (not shown) used to remove spacer 90 from humeral stem 36 whereby, upon threading of the threaded end of the retrieval instrument through threaded bore 108, the threaded end will bottom out against the bottom of tapered bore 60 of humeral stem 36 to disengage spacer 90 from humeral stem 36.

Figure 13:
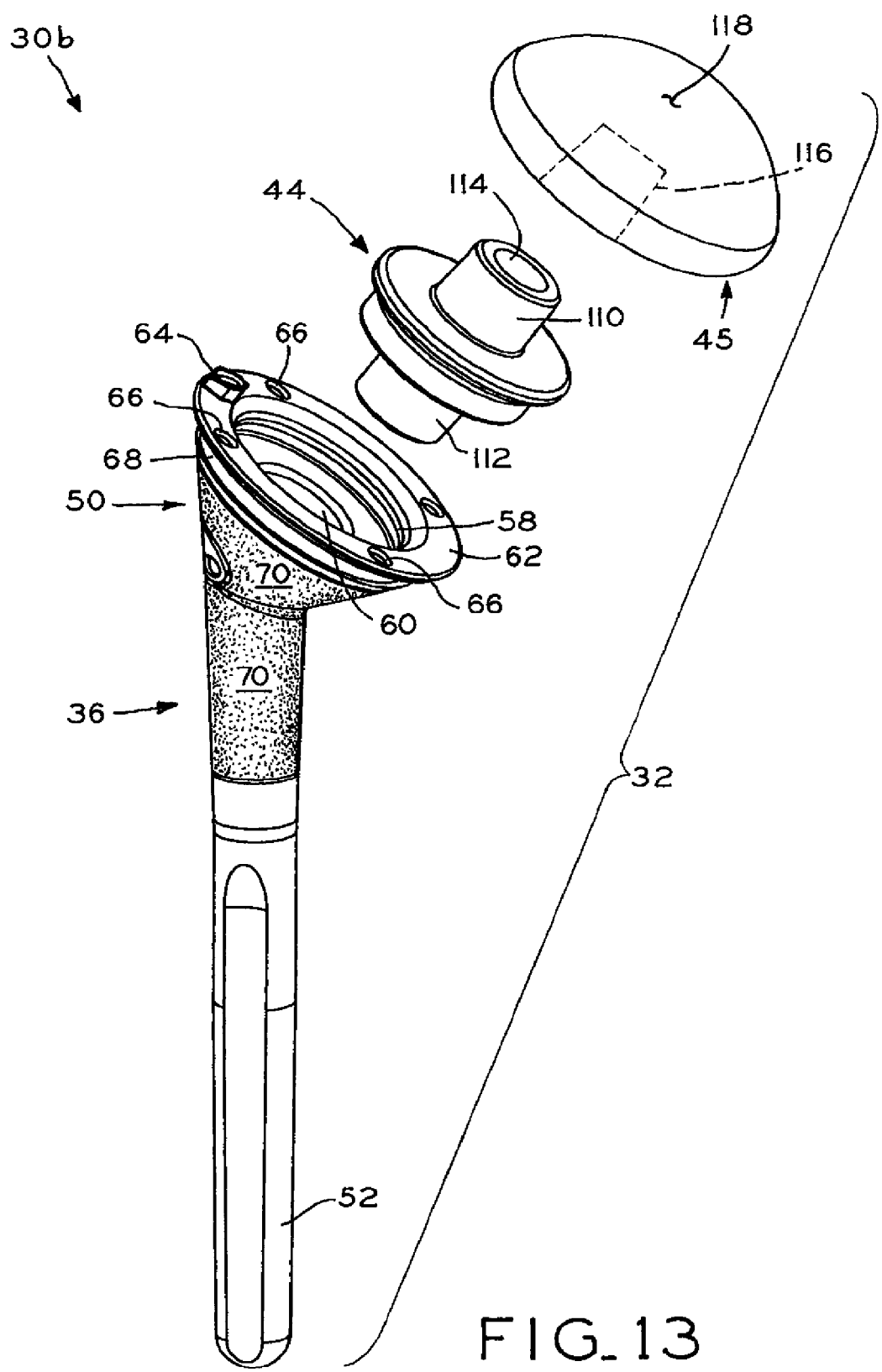
FIG. 13 is an exploded view of the humeral stem, an adapter insert, and a humeral head.

Referring to FIGS. 12A and 12B, distal and proximal views of adapter insert 44 are shown, which may be used with humeral stem 36 to provide an interface with humeral head 45 to configure humeral stem 36 for use in a conventional total shoulder arthroplasty or a hemi shoulder arthroplasty. The proximal end of adapter insert 44 includes a first tapered stem 110 and the distal end of adapter insert 44 includes a second tapered stem 112, with a central bore 114 extending therethrough. Referring additionally to FIGS. 13 and 14, when the distal end of adapter insert 44 is received within internal cavity 54 of humeral stem 36, second tapered stem 112 of adapter insert 44 is lockingly fittable within tapered bore 60 of humeral stem 36. Thereafter, humeral head 45, which includes a distal tapered bore 116 and proximal convex articulating surface 118 may be fitted onto first tapered stem 110 of adapter insert 44 to complete the humeral assembly. In use, as described above, convex articulating surface 118 of humeral head 45 articulates against a conventional glenoid component (not shown) in a conventional total shoulder arthroplasty, or articulates against the intact glenoid of the scapula in a hemi shoulder arthroplasty. Adapter insert 44 additionally includes thread 120 (FIG. 12A) within central bore 114 to enable adapter insert 44 to be removed from humeral stem 36 using a threaded retrieval instrument (not shown) analogous to the manner described above with respect to the removal of spacer 90 from humeral stem 36.

Figure 23:
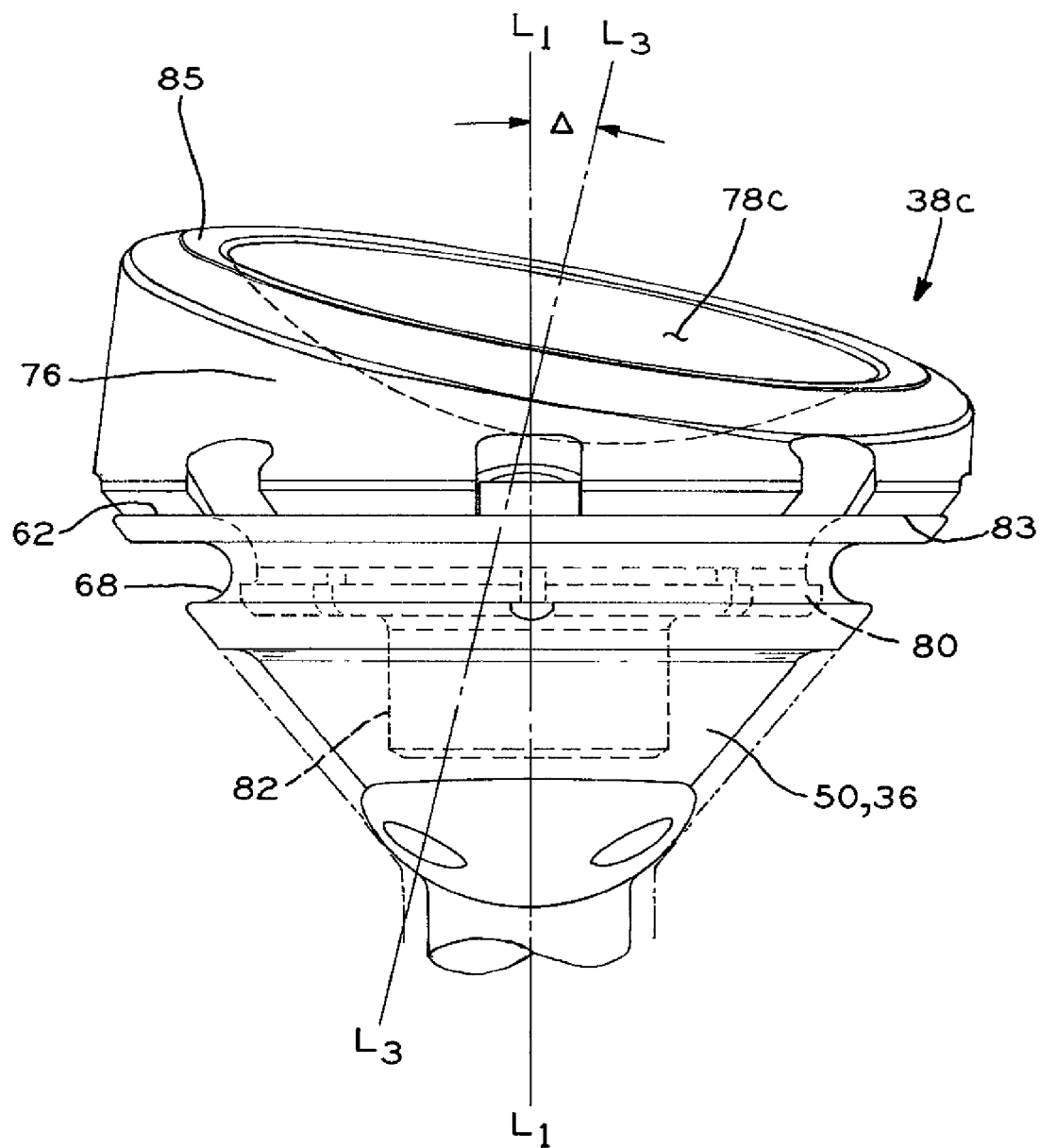
FIG. 23 is partial sectional view through an anterior/posterior plane, showing the connection between the humeral stem and an articulating liner according to a further embodiment.
Figure 24:
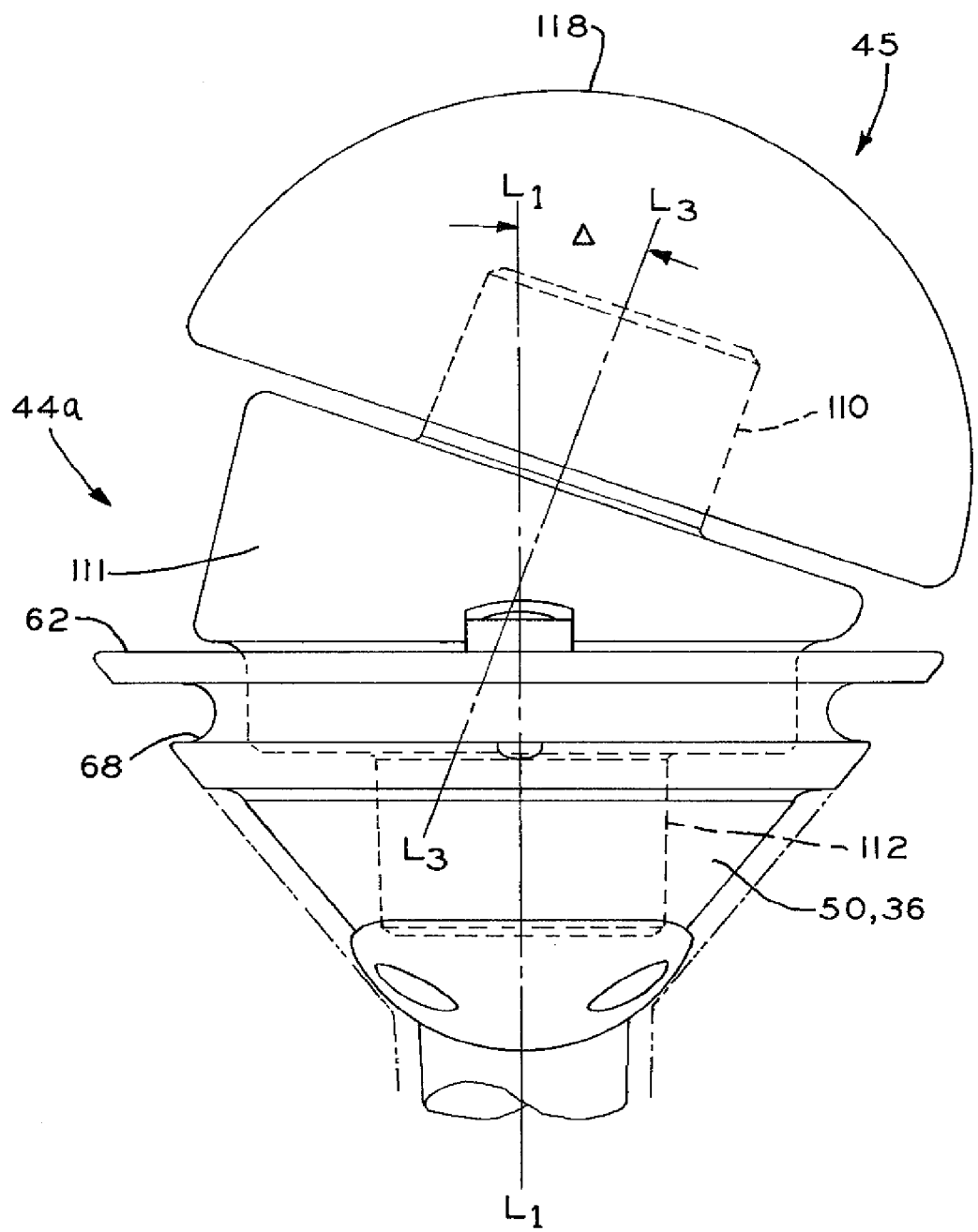
FIG. 24 is a partial sectional view through an anterior/posterior plane, showing the connection between the humeral stem and an adapter insert according to a further embodiment.

As discussed below, the articulating liners and the adapter inserts of the present shoulder implant system may also include an anteversion or retroversion feature. Referring to FIGS. 23 and 24, further embodiments of an articulating liner and an adapter insert are shown, which are each angled in an anterior/posterior plane with respect to the longitudinal axis $L_1$-$L_1$ of humeral stem 36 to provide anteversion or retroversion.

Referring to FIG. 23, an articulating liner 38c is shown attached to humeral stem 36 which, except as described below, is identical to articulating liner 38 described above. Body 76 of articulating liner 38c includes a concave articulating surface 78c which is oriented at an angle $\Delta$ in an anterior/posterior plane with respect to longitudinal axis $L_1$-$L_1$ of humeral stem 36. Specifically, a line $L_3$-$L_3$, which is perpendicular to articulating surface 78c and passes through the center thereof, defines angle $\Delta$ with respect to longitudinal axis $L_1$-$L_1$ of humeral stem 36. Angle $\Delta$ may define an anterior-facing orientation of articulating surface 78c for anteversion or, as shown in FIG. 23, angle $\Delta$ may define a posterior-facing orientation of articulating surface 78c for retroversion. Angle $\Delta$ may be as small as about 1, 5, or 10 degrees, or may as large as about 20, 25, or 30 degrees, or may be sized at any one degree increment therebetween, for example. In the embodiment of FIG. 23, angle $\Delta$ is about 20 degrees. Additionally, as shown in FIG. 23, the articulating liners 38 disclosed herein may include both the foregoing anteversion or retroversion angle $\Delta$ in an anterior/posterior plane with respect to longitudinal axis $L_1$-$L_1$ of humeral stem 36, as well as the above-described angle $\gamma$ in a medial/lateral plane with respect to the longitudinal axis $L_1$-$L_1$ of humeral stem 36. In this manner, articulating liner 38c can be used to provide anteversion or retroversion in a "reverse" total shoulder arthroplasty.

Referring to FIG. 24, adapter insert 44a is shown attached to humeral stem 36 which, except as described below, is identical to adapter insert 44 described above. Adapter insert 44a includes an angled body portion 111 which positions first tapered stem 110 of adapter insert 44a at an angle $\Delta$ in an anterior/posterior plane with respect to longitudinal axis $L_1$-$L_1$ of humeral stem 36. Specifically, a line $L_3$-$L_3$, which extends along the longitudinal axis of adapter insert 44a and tapered stem 110, defines angle $\Delta$ with respect to longitudinal axis $L_1$-$L_1$ of humeral stem 36. Angle $\Delta$ may define an anterior-facing orientation of first tapered stem 110 for anteversion or, as shown in FIG. 24, angle $\Delta$ may define a posterior-facing orientation of first tapered stem 110 for retroversion. Angle $\Delta$ may be as small as about 1, 5, or 10 degrees, or may as large as about 20, 25, or 30 degrees, or may be sized at any one degree increment therebetween, for example. In the embodiment of FIG. 23, angle $\Delta$ is about 20 degrees. Humeral head 45, having convex articulating surface 118, is mounted to first tapered stem 110 of adapter insert 44a in the manner described above, and is oriented according to the anteversion or retroversion angle defined by adapter insert 44a. Additionally, similar to the articulating liners 38 disclosed herein, adapter insert 44a may include both the foregoing anteversion or retroversion angle $\Delta$ in an anterior/posterior plane with respect to longitudinal axis $L_1$-$L_1$ of humeral stem 36, as well as an angle in a medial/lateral plane with respect to the longitudinal axis $L_1$-$L_1$ of humeral stem 36. In this manner, adapter insert 44a can be used to provide anteversion or retroversion in a conventional total shoulder arthroplasty or in a hemi shoulder arthroplasty.

Advantageously, humeral stem 36 provides a humeral component which serves as a universal humeral implant platform that may be used with the various modular components in the manner described above to configure humeral stem 36 for use in a "reverse" total shoulder arthroplasty, a conventional total shoulder arthroplasty, or a hemi shoulder arthroplasty. Thus, once the humeral stem 36 is implanted within the proximal humerus as shown in FIG. 3, the humeral stem 36 may be configured for a "reverse" total shoulder arthroplasty as shown in FIGS. 1 and 6A-11, or a conventional total shoulder arthroplasty or hemi shoulder arthroplasty as shown in FIGS. 2 and 12A-14 according to patient needs by using the components described above.

Also, once implanted, humeral stem 36 may remain implanted throughout any necessary revision procedures, allowing a surgeon to perform any revisions as needed by replacing one more of the various modular components described above without the need to replace humeral stem 36 itself. For example, if a patient initially has a hemi shoulder arthroplasty and later is in need of a revision to receive a "reverse" total shoulder arthroplasty, humeral head 45 is removed, followed by adapter insert 44. Thereafter, an articulating liner 38 and optionally, a spacer 90, are attached to humeral stem 36 in the manner described above without the need to remove humeral stem 36 from the patient's humerus. A similar procedure may be used to convert a conventional total shoulder arthroplasty to a "reverse" total shoulder arthroplasty.

One particular advantage of humeral stem 36 is that the proximal surface thereof lies substantially along the resection cut line $L_2$-$L_2$ of the resected humerus as discussed above. Thus, the various modular components disclosed herein may be attached, removed, and/or replaced onto the implanted humeral stem 36 above the resection cut line $L_2$-$L_2$ without the need for removing bone around the proximal humerus H and/or replacing or modifying the location of the implanted humeral stem 36 in the humerus H.

Figure 17:
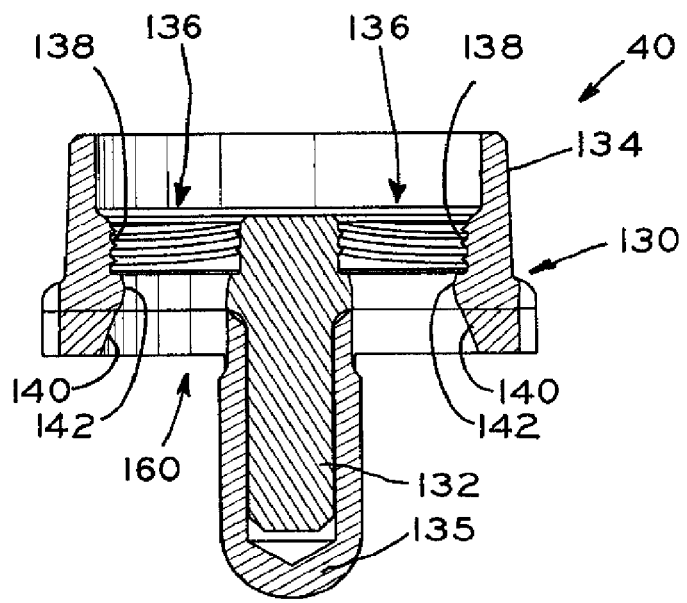
FIG. 17 is a sectional view of the glenoid base.
Figure 18:
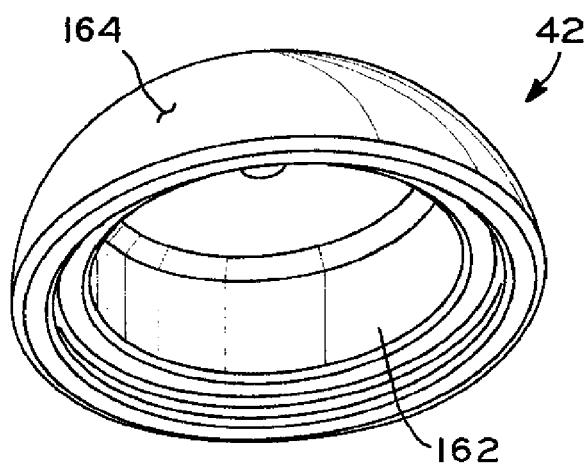
FIG. 18 is a perspective view of the medial side of the glenosphere.
Figure 20:
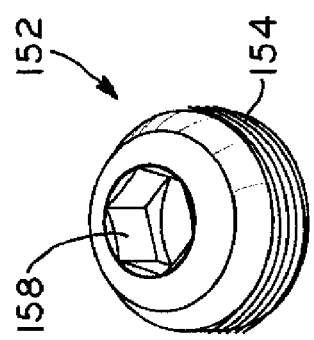
FIG. 20 is a first perspective view of a screw lock.
Figure 21:
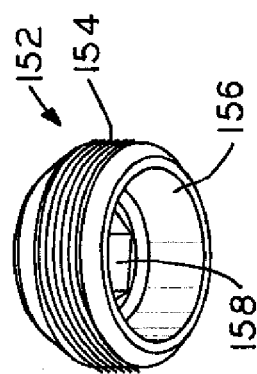
FIG. 21 is a second perspective view of a screw lock.
Figure 19:
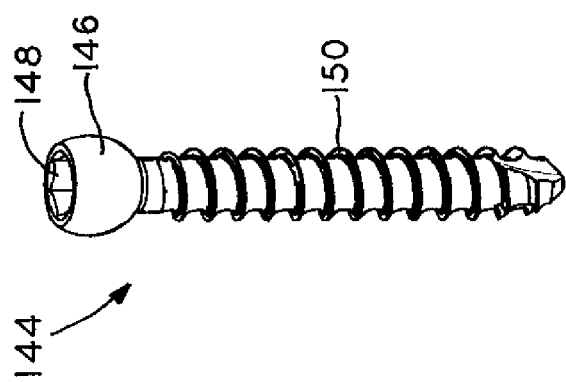
FIG. 19 is a perspective view of a screw.
Figure 22:
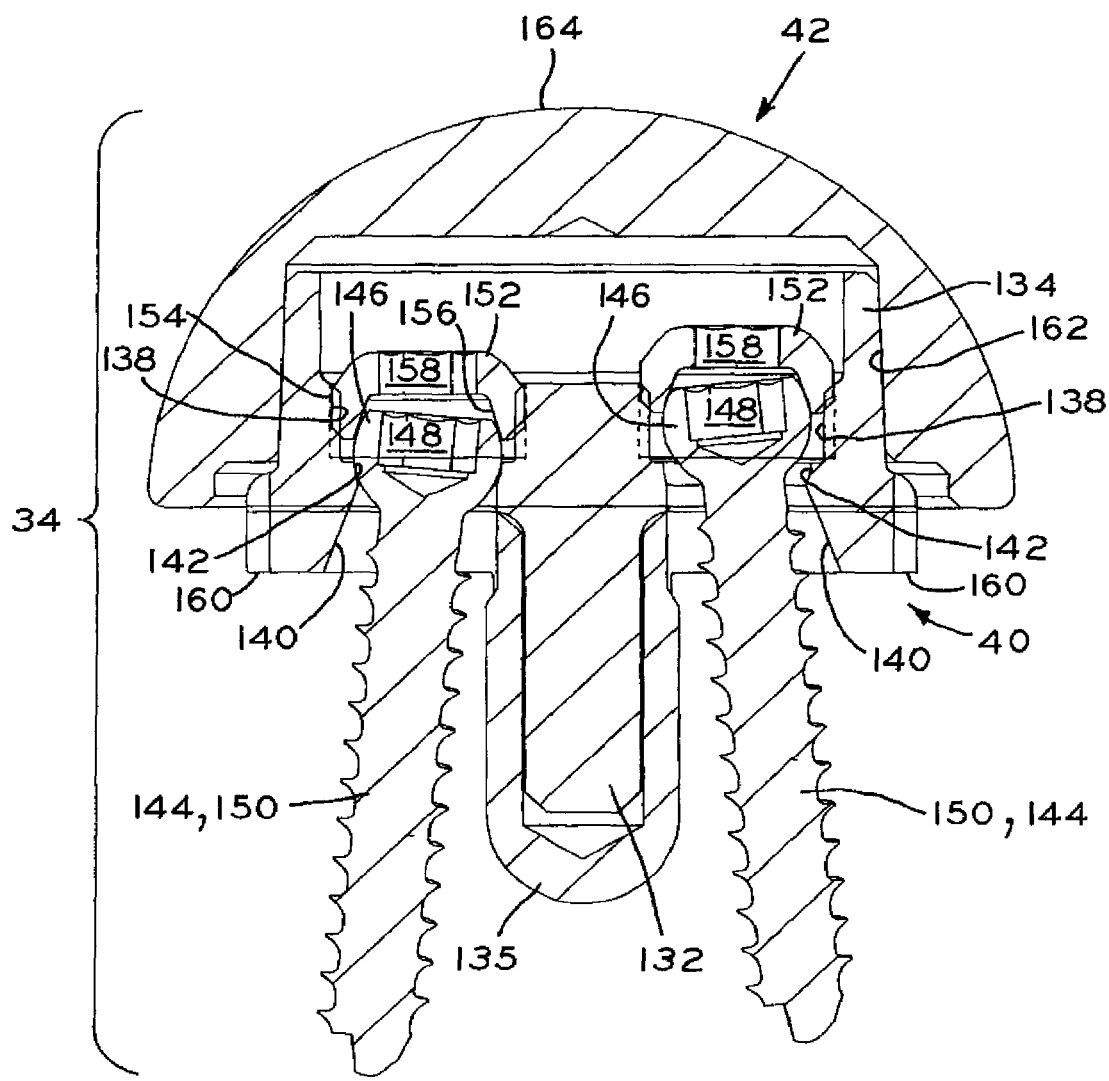
FIG. 22 is a sectional view through the glenoid component, showing connection between the glenoid base, screws, and glenosphere, and further showing a screw and a screw head lock in a locked position on the left and a screw and a screw head lock in an unlocked position on the right.

Referring to FIGS. 15-22, glenoid component 34 (FIG. 22) is shown, which generally includes a glenoid base 40, shown in FIGS. 15-17 and 22, and glenosphere 42, shown in FIGS. 18 and 22. Referring to FIGS. 15-17, glenoid base 40 includes a body 130 which may be made of a suitable biocompatible metal such as titanium, for example, and includes stem portion 132 (FIG. 17) projecting from a medial side thereof, and a tapered annular wall 134 projecting from a lateral side thereof. The medial side of body 130 of glenoid base 40, including stem portion 132, may include a pad or coating portion 135 of the highly porous biomaterial described above, produced using Trabecular Metal™ technology available from Zimmer, Inc., of Warsaw, Ind., to promote bone ingrowth from the glenoid into and around glenoid base 40 to thereby osseointegrate glenoid base 40 with the glenoid. Typically, the glenoid is prepared for attachment of glenoid component 34 by preparing a bore in the glenoid for receipt of stem portion 132 of glenoid body 130, and by reaming the glenoid with a reamer (not shown) to prepare a substantially flat, planar surface on the glenoid to which the substantially flat, planar medial side of body 130 may be fitted, as described below.

Body 130 of glenoid base 40 includes a pair of bores 136 therethrough which, as best shown in FIG. 17, include first, threaded portions 138 and second portions 140 which are tapered to open outwardly toward the medial side of glenoid base 40. Bores 136 additionally include screw head seats 142 located between first and second portions 138 and 140 of bores 136. As shown, screw head seats 142 have an at least partially spherical shape, but may also have an angled or tapered profile. To secure glenoid base 40 to the glenoid, a pair of polyaxial screws 144 are provided, shown in FIG. 19, each including a substantially spherical head 146 with tool engagement structure, such as a polygonal fitting 148, and a threaded shank 150. Screw locks 152, shown in FIGS. 20 and 21, are also provided which, as described below, cooperate with threaded portions 138 of bores 136 and with heads 146 of screws 144 to lock the positions of screws 144. Each screw lock 152 generally includes an external thread 154, a semispherical concave seat 156, and instrument engagement structure such as a polygonal fitting 158.

Referring to FIG. 22, glenoid base 40 is shown with a screw 144 and screw head lock 152 in a locked position on the left and a screw 144 and screw head lock 152 in an unlocked position on the right. To secure glenoid base 40 to the prepared glenoid, each screw 144 is inserted using a suitable instrument (not shown) through a respective bore 136 in body 130 and is threaded into a pre-tapped bore in the glenoid. Tapered second portions 140 of bores 136 accommodate polyaxial positioning of screws 144 up to an angle of 30° from the longitudinal axis of glenoid base 40 as defined along stem portion 132 thereof. Advantageously, the ability of glenoid base 40 to accommodate polyaxial positioning of screws 144 allows the surgeon to determine optimum angles of screws 144 needed to conform to the anatomy of the patient and/or to most effectively take advantage of available bone stock to anchor glenoid base 40 to the glenoid. Thereafter, referring to the left of FIG. 22, screw locks 152 are threaded into threaded first portions 138 of bores 136 using a suitable instrument (not shown) to firmly engage seats 156 of screw head locks 152 against heads 146 of screws 144, thereby firmly pressing screw heads 146 against seats 142 within bores 136 to locking screw heads 146 in a selected fixed position and in turn to fix the positions of screws 144 with respect to glenoid base 40.

Advantageously, as may be seen in FIGS. 17 and 22, because body 130 of glenoid base 40 includes tapered second portions 140 of bores 136 to accommodate polyaxial positioning of screws 144, with screw seats 142 recessed into the medial side of body 130 of glenoid base 40, glenoid base 40 may include a substantially planar medial side 160, with tapered second portions 140 of bores 136 accommodating polyaxial positioning of screws 144. The planar medial side 160 of glenoid base 40 allows glenoid base 40 to be seated against a planar surface of the glenoid which may be prepared with a planar reamer (not shown), and eliminates the need for boss portions or other protuberances projecting from the medial side of glenoid base 40 to accommodate polyaxial positioning of screws 144, which would require additional glenoid preparation steps to accommodate.

Referring to FIGS. 18 and 22, glenosphere 42 generally includes a medial side having a tapered interior bore 162 extending therein, which may be aligned with a longitudinal axis of glenosphere 42 or may be offset with respect to the longitudinal axis of glenosphere 42. Glenosphere 42 additionally includes a lateral side having a convex articulating surface 164. Glenosphere 42 may be provided in a variety of different sizes, such as with varying diameters, varying heights, and varying offsets for internal bore 162 to enable a surgeon to select an optimal glenosphere needed for the anatomy of a particular patient. The glenosphere is fitted onto glenoid base 40 by lockingly fitting tapered bore 162 of glenosphere 42 onto the cooperatively tapered annular wall 134 of glenoid base 40. Advantageously, the foregoing attachment between bore 162 of glenosphere 42 and annular wall 134 of glenoid base 40 allows glenosphere 42 to have a substantially smooth, uninterrupted articulating surface 164 which lacks an opening therein for receipt of a fastener, for example.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A humeral implant component for use in a reverse total shoulder arthroplasty, comprising:
    a stem that includes a stem portion extending toward a distal end of the stem and a head portion at a proximal end of the stem, said head portion including a head portion cavity with a first diameter portion and an annular rib element that projects into the head portion cavity from said first diameter portion to create a second diameter portion in the head portion cavity, said second diameter portion having a smaller diameter than said first diameter portion; and
    an articulating liner, the articulating liner including a first end that is receivable in said head portion cavity for axially securing said articulating liner to said head portion, said articulating liner being substantially wedge-shaped with an annular upper surface opposite an annular lower surface and with a concave articulating surface extending from said annular upper surface for articulating against a convex surface of a glenoid component, said annular upper surface and said annular lower surface defining an angle therebetween, said annular upper surface being angled between about 55 degrees and about 70 degrees with respect to a longitudinal axis of said stem, said annular lower surface being angled between about 35 degrees and about 55 degrees with respect to said longitudinal axis of said stem, wherein the first end of the articulating liner includes an annular engagement structure configured to extend into the first diameter portion of the head portion cavity behind said annular rib element so as to engage said annular rib element for axially securing the articulating liner to the head portion
    wherein the head portion cavity includes a tapered bore providing a third diameter portion with a diameter that is smaller than said second diameter portion, and wherein the first end of the articulating liner further includes a post projecting beyond said annular engagement structure for receipt in said tapered bore for axially securing said articulating liner to said head portion.

2. The humeral implant component of claim 1, wherein said annular lower surface is angled between about 50 degrees and about 55 degrees with respect to said longitudinal axis.

3. The humeral implant component of claim 1, wherein the head portion is a separate piece that is separable from the stem portion.

4. The humeral implant component of claim 1, further comprising a metallic spacer connecting the articulating liner to the stem.

5. The humeral implant component of claim 1, wherein said post is shaped to provide an interference fit within the tapered bore of the head portion cavity.

6. The humeral implant component of claim 1, wherein said annular engagement structure comprises a plurality of spring fingers.

7. The humeral implant component of claim 1, wherein the stem includes a hub section providing a suture hole in a proximal region of the stem.

8. A humeral implant component for use in a reverse total shoulder arthroplasty, comprising:
    a stem that includes a stem portion extending toward a distal end of the stem, the stem portion defining a longitudinal axis, said stem further including a separable head piece that is joined to the stem portion so as to provide an enlarged head portion at a proximal end of the stem, said enlarged head portion including a proximal surface that is angled between about 35 degrees and about 55 degrees with respect to said longitudinal axis, said enlarged head portion including a head portion cavity in which an articulating liner can be received, said head portion cavity including a first annular engagement structure disposed in the head portion cavity;
    an articulating liner receivable in said head portion cavity for securing the articulating liner to the enlarged head portion, said articulating liner including an upper surface from which a concave articulating surface extends for articulating against a convex surface of a glenoid component, said upper surface being angled between about 55 degrees and about 70 degrees with respect to said longitudinal axis, wherein the articulating liner includes a second annular engagement structure projecting from an annular lower surface, said second annular engagement structure configured to engage said first annular engagement structure in the head portion cavity of the enlarged head portion for axially securing the articulating liner to the enlarged head portion; and
    a metallic spacer that includes a spacer cavity with a third annular engagement structure disposed in the spacer cavity,
    wherein said articulating liner also is receivable in said spacer cavity, the second annular engagement structure of the articulating liner configured to engage the third annular engagement structure in the spacer cavity for axially securing the articulating liner to the metallic spacer, a first end of the articulating liner including a post that projects beyond the second annular engagement structure for receipt in a tapered bore in the spacer cavity for axially securing said articulating liner to said metallic spacer, whereby said articulating liner is selectively axially securable to said metallic spacer and said enlarged head portion so that said metallic spacer can be used to modularly secure said articulating liner to said enlarged head portion.

9. The humeral implant component of claim 8, wherein said proximal surface is angled between about 50 degrees and about 55 degrees with respect to said longitudinal axis.

10. The humeral implant component of claim 8, wherein the articulating liner includes an annular lower surface that is disposed substantially parallel to the proximal surface of said enlarged head portion.

11. The humeral implant component of claim 8, wherein the third annular engagement structure comprises an annular rib element for cooperating with the second annular engagement structure of the articulating liner for axially securing said articulating liner to the metallic spacer.

12. The humeral implant component of claim 8, wherein the second annular engagement structure of the articulating liner comprises a plurality of spring fingers.

13. A humeral implant component for use in a reverse total shoulder arthroplasty, comprising:
- a stem that includes a stem portion extending toward a distal end of the stem, the stem portion defining a longitudinal axis, said stem further including a separable head piece that is joined to the stem portion so as to provide an enlarged head portion at a proximal end of the stem, said enlarged head portion including a proximal surface adapted to be disposed substantially parallel to a resection cut line of a humerus when said humeral implant component is implanted in the humerus;
- an articulating liner disposed proximate the proximal end of the stem, said articulating liner including an annular lower surface adapted to be disposed substantially parallel to the proximal surface of said head portion when said humeral implant component is implanted within the humerus, said articulating liner also including an annular upper surface from which a concave articulating surface extends for articulating against a convex surface of a glenoid component, said upper surface being angled between about 55 degrees and about 70 degrees with respect to said longitudinal axis, the articulating liner including a first annular engagement structure that projects beyond said annular lower surface, the articulating liner further including a post that projects beyond said first annular engagement structure; and
- a metallic spacer connecting the articulating liner to the head portion, said metallic spacer including a spacer cavity with a second annular engagement structure and a tapered bore disposed in the spacer cavity,
- wherein the articulating liner is received in the spacer cavity with the first annular engagement structure of the articulating liner engaging the second annular engagement structure of the spacer cavity and with the post of the articulating liner received in the tapered bore of the spacer cavity for axially securing said articulating liner to said metallic spacer.

14. A humeral implant component for use in a reverse total shoulder arthroplasty, comprising:
- a stem that includes a stem portion extending toward a distal end of the stem and a separable head piece that is joined to the stem portion so as to provide an enlarged head portion at a proximal end of the stem, said enlarged head portion including a head portion cavity;
- an articulating liner receivable in said head portion cavity for axially securing said articulating liner to said enlarged head portion, said articulating liner having an annular upper surface from which a concave articulating surface extends for articulating against a convex surface of a glenoid component; and
- a metallic spacer including a spacer cavity,
- wherein said head portion cavity incorporates an annular engagement structure dimensionally replicating an annular engagement structure disposed in said spacer cavity,
- wherein said spacer includes a post receivable in a bore of said head portion cavity for axially securing said metallic spacer to said stem,
- wherein said articulating liner also is receivable in said spacer cavity for axially securing said articulating liner to said metallic spacer, the articulating liner including a post capable of being interchangeably received in (i) the bore of said head portion cavity for axially securing said articulating liner to said stem and (ii) a bore of said spacer cavity for axially securing said articulating liner to said metallic spacer, whereby said articulating liner is selectively axially securable to said metallic spacer and said head portion so that said spacer can be used to modularly secure said articulating liner to said head portion.

15. The humeral implant component of claim 14, wherein said head portion cavity incorporates an annular rib element dimensionally replicating an annular rib element disposed in said spacer cavity.

16. The humeral implant component of claim 14, wherein said annular upper surface is angled between about 55 degrees and about 70 degrees with respect to a longitudinal axis of said stem portion when the articulating liner is disposed at the proximal end of the stem.

17. The humeral implant component of claim 16, wherein said annular upper surface is angled between about 60 degrees and about 65 degrees with respect to said longitudinal axis when the articulating liner is disposed at the proximal end of the stem.

18. The humeral implant component of claim 14, wherein said articulating liner is substantially wedge-shaped between said annular upper surface and an annular lower surface, said annular upper surface and said annular lower surface defining an angle therebetween.

19. The humeral implant component of claim 18, wherein said annular upper surface is angled between about 55 degrees and about 70 degrees with respect to a longitudinal axis of said stem portion when the articulating liner is disposed at the proximal end of the stem.

20. The humeral implant component of claim 19, wherein said annular lower surface is angled between about 35 degrees and about 55 degrees with respect to said longitudinal axis when the articulating liner is disposed at the proximal end of the stem.

21. A humeral implant component for use in a reverse total shoulder arthroplasty, comprising:
- a stem that includes a stem portion extending toward a distal end of the stem and a head portion at a proximal end of the stem;
- a spacer secured to said head portion and including a spacer cavity incorporating a first annular engagement structure and a tapered bore that is spaced distally from said first annular engagement structure in the spacer cavity; and
- an articulating liner, the articulating liner including a first end that is received in said spacer cavity, the first end of the articulating liner including a second annular engagement structure for engaging said first annular engagement structure in said spacer cavity, the first end of the articulating liner further including a post that projects beyond said second annular engagement structure for receipt in said tapered bore to provide an interference fit between said post and said tapered bore for axially securing the articulating liner to the spacer, said articulating liner having an annular upper surface from which a concave articulating surface extends for articulating against a convex surface of a glenoid component.

22. The humeral implant component of claim 21, wherein said annular upper surface is angled between about 55 degrees and about 70 degrees with respect to a longitudinal axis of said stem portion.

23. The humeral implant component of claim 22, wherein said articulating liner is substantially wedge-shaped between said annular upper surface and an annular lower surface, said annular upper surface and said annular lower surface defining an angle therebetween.

24. The humeral implant component of claim 21, wherein the head portion is separable from the stem portion.

25. The humeral implant component of claim 21, wherein said articulating liner is substantially wedge-shaped between said annular upper surface and an annular lower surface, said annular upper surface and said annular lower surface defining an angle therebetween.

26. The humeral implant component of claim 25, wherein said second annular engagement structure comprises a plurality of spring fingers.

27. A humeral implant component for use in a reverse total shoulder arthroplasty, comprising:
   a stem that includes a stem portion extending toward a distal end of the stem and an enlarged head portion at a proximal end of the stem, said enlarged head portion including a head portion internal cavity in which an articulating liner can be received, said head portion internal cavity including a first annular engagement structure disposed in the head portion internal cavity;
   an articulating liner receivable in said head portion internal cavity for securing the articulating liner to the enlarged head portion, said articulating liner being substantially wedge-shaped with an annular lower surface opposite an annular upper surface and with a concave articulating surface extending from said annular upper surface for articulating against a convex surface of a glenoid component, wherein said annular upper surface and said annular lower surface define an angle therebetween, and wherein the articulating liner includes a second annular engagement structure projecting from said annular lower surface, said second annular engagement structure configured to engage said first annular engagement structure in the head portion internal cavity of the enlarged head portion for axially securing the articulating liner to the enlarged head portion; and
   a metallic spacer that includes a spacer cavity with a third annular engagement structure disposed in the spacer cavity, the spacer including a post receivable in a bore of said head portion internal cavity for axially securing said metallic spacer to said stem,
   wherein said articulating liner also is receivable in said spacer cavity, the second annular engagement structure of the articulating liner configured to engage the third annular engagement structure in the spacer cavity for axially securing the articulating liner to the metallic spacer, the articulating liner including a post capable of being interchangeably received in (i) the bore of the head portion internal cavity for axially securing said articulating liner to said stem and (ii) a bore of said spacer cavity for axially securing said articulating liner to said metallic spacer, whereby said articulating liner is selectively axially securable to said metallic spacer and said enlarged head portion so that said metallic spacer can be used to modularly secure said articulating liner to said enlarged head portion.

28. The humeral implant component of claim 27, wherein said annular upper surface is angled being between about 55 degrees and about 70 degrees with respect to a longitudinal axis of said stem portion.

29. The humeral implant component of claim 27, wherein the first annular engagement structure and the third annular engagement structure each comprise an annular rib element.

30. The humeral implant component of claim 29, wherein the second annular engagement structure comprises a plurality of spring fingers.

* * * * *